United States Patent
Mukherjee et al.

(10) Patent No.: US 10,231,996 B2
(45) Date of Patent: Mar. 19, 2019

(54) BIOCAMPATIBLE POLYMER COATED SILVER PRUSSIAN BLUE NANOPARTICLES (SPB-NPS: AG$_3$[FE(CN)$_6$])

(71) Applicant: COUNCIL OF SCIENTIFIC & INDUSTRIAL RESEARCH, New Delhi (IN)

(72) Inventors: Sudip Mukherjee, Hyderabad (IN); Chitta Ranjan Patra, Hyderabad (IN)

(73) Assignee: COUNCIL OF SCIENTIFIC & INDUSTRIAL RESEARCH, New Delhi (IN)

(*) Notice: Subject to any disclaimer, the term of this patent is extended or adjusted under 35 U.S.C. 154(b) by 0 days.

(21) Appl. No.: 15/049,604

(22) Filed: Feb. 22, 2016

(65) Prior Publication Data

US 2016/0243163 A1 Aug. 25, 2016

(30) Foreign Application Priority Data

Feb. 23, 2015 (IN) .......................... 0502/DEL/2015

(51) Int. Cl.
| | |
|---|---|
| A61K 33/38 | (2006.01) |
| A01N 59/16 | (2006.01) |
| A01N 25/26 | (2006.01) |
| A61K 9/51 | (2006.01) |
| A01N 25/28 | (2006.01) |
| A61K 9/00 | (2006.01) |

(52) U.S. Cl.
CPC .............. *A61K 33/38* (2013.01); *A01N 25/28* (2013.01); *A01N 59/16* (2013.01); *A61K 9/5138* (2013.01); *A61K 9/5146* (2013.01); *A61K 9/5192* (2013.01); *A61K 9/0019* (2013.01)

(58) Field of Classification Search
CPC ......... A01N 25/28; A01N 59/16; A61K 33/38
See application file for complete search history.

(56) References Cited

U.S. PATENT DOCUMENTS

| | | |
|---|---|---|
| 7,678,188 B2 | 3/2010 | Kawamoto et al. |
| 8,349,221 B2 | 1/2013 | Kawamoto et al. |
| 2008/0213189 A1* | 9/2008 | Lee .................. A61K 47/48215 424/9.32 |
| 2014/0037552 A1* | 2/2014 | Mathe .................... A61K 49/08 424/9.4 |

FOREIGN PATENT DOCUMENTS

EP 2116511 A1 11/2009

OTHER PUBLICATIONS

Uemura et al. (Prussian Blue Nanopartiles Protected by Poly(vinylpyrolidone) JACS 2003, 125 7814-7815).*
Chen et al. (Langmuir Article 2010, 26 (16), 13183-13194).*
Cheng et al. (Biomaterials 35 (2014) 9844-9852).*
Kumar et al. (Nature Materials 2008 1-6 IDS).*
2004—"The use of nanocrystals in biological detection" —Paul Alivisatos—Nature: Biotechnology.
2004—"In vivo cancer targeting and imagin with semiconductor quantum dots" —Xiaohu Gao, et. al—Nature: Biotechnology.
2008—"Silver-nanoparticle-embedded antimicrobial paints based on vegetable oil" —Ashavani Kumar, et. al—Nature: Materials.
2008—"Nanomedicine Captures Cardiovascular Disease" —Willem Mulder, et. al—Arteioscler Thromb Vascular Biology.
2008—"Targeted Delivery of Gmcitabine to Pancreatic Adenocarcinoma Using Cetuximab as a Targeting Agent" —Chitta Ranjan Patra, et. al—Cancer Research.
2011—"Reactive Oxygen Species Driven Angiogenesis by Inorganic Nanorods" —Chitta Ranjan Patra, et. al.
2004—"Biological synthesis of triangular gold nanoprisms" —S. Shiv Shankar, et. al—Nature: Materials.
2014—"Manganese-containing Prussian blue nanoparticles for imaging of pediatric brian tumors" —Matthieu Dumont, et. al—International Journal of Nanomedicine.
2005—"Synthesis, characterization and immobilization of Prussion blue nanoparticles. A potential tool for biosensing devices" —Pablo Fiorito et. al—Chemical Communication.
2004—"Soluble or Insoluble Prussian Blue for Radiocesium and Thallium Poisoning?" —Dennis Thompson, et. al—The Annals of Pharmacotherapy.
2014—"Prussian blue coated gold nanoparticles for simultaneous photoacoustic/CT biomodal imaging and photothermal ablation of cancer" —Lijia Jing, et. al—Biomaterials.
2013—"Dual anticancer drug/superparamagnetic iron oxide-loaded PLGA-based nanoparticles for cancer therapy and magnetic resonance imaging" —N. Scheich, et. al—International Journal of Pharmaceutics.

* cited by examiner

*Primary Examiner* — Anna R Falkowitz
(74) *Attorney, Agent, or Firm* — Banner & Witcoff, Ltd.

(57) ABSTRACT

The present invention relates to highly biocompatible or nontoxic PVP (poly(n-vinyl-2-pyrrolidone) coated silver prussian blue nanoparticles (SPB-NPS: Ag$_3$[Fe(CN)$_6$] where PVP acts as stabilizing or capping agent. The as-synthesized nanoparticles (SPB-NPs) have been thoroughly characterized by several analytical tools. The SPB-NPs are highly stable for more than two weeks towards different physiological buffers or solutions with different pH (pH=6, ~7.4 & ~8). These nanoparticles (SPB-NPs) exhibit biocompatibility towards various normal cells (HUVEC, CHO, & ECV304) but show significant inhibition of proliferation of different cancer cells in vitro and tumor growth in C57/BL6/J mice model (aggressive murine melanoma cancer model: B16F10). Additionally, the SPB-NPs show excellent antibacterial activity towards gram-negative (*E. coli*) and gram-positive (*B. subtilis*) bacteria. Consider all results together; these biocompatible SPB-NPs would be potentially useful for the development towards alternative anti-cancer agent as well as anti-bacterial agent in near future.

20 Claims, 21 Drawing Sheets

Fig.4 Comparison of TEM images and size distribution

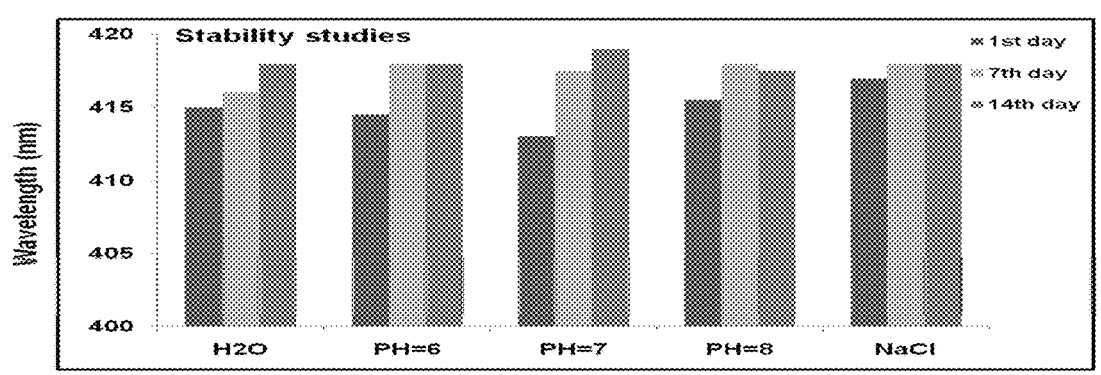

Fig.7.a-d
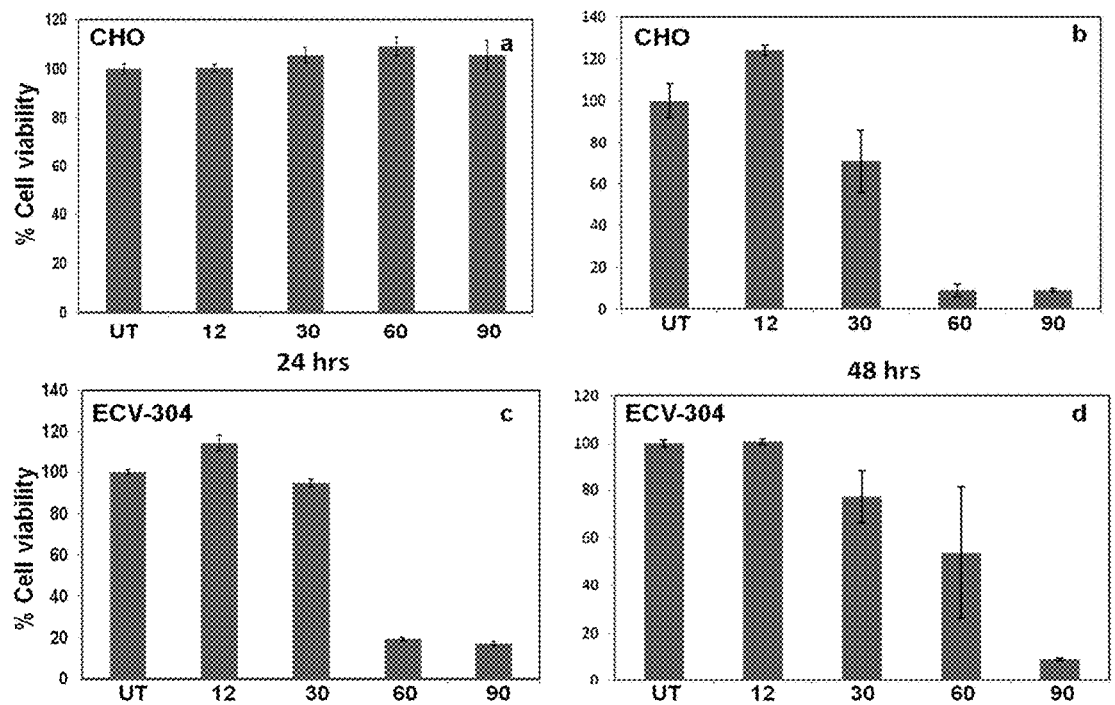
Fig.7.e
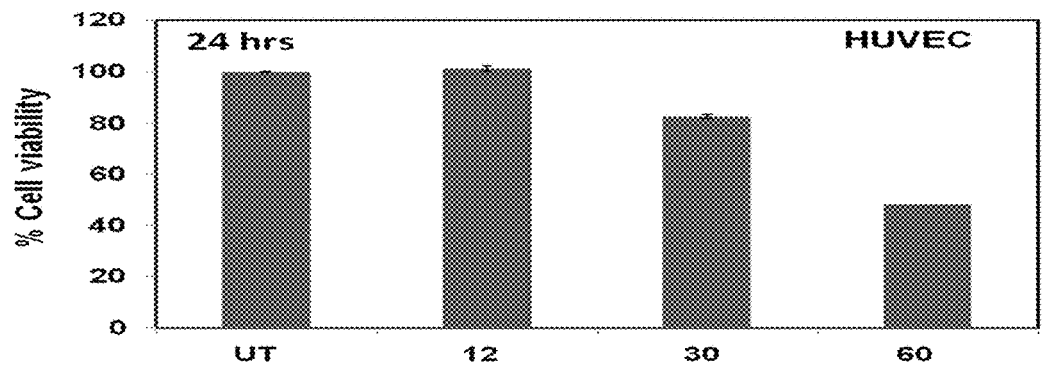

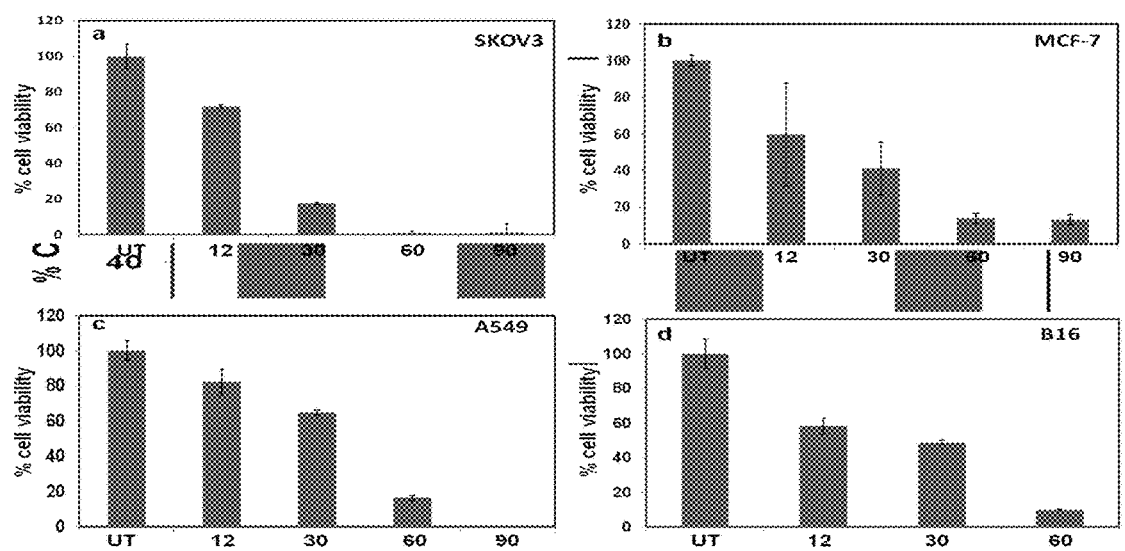
Fig.8.a-d

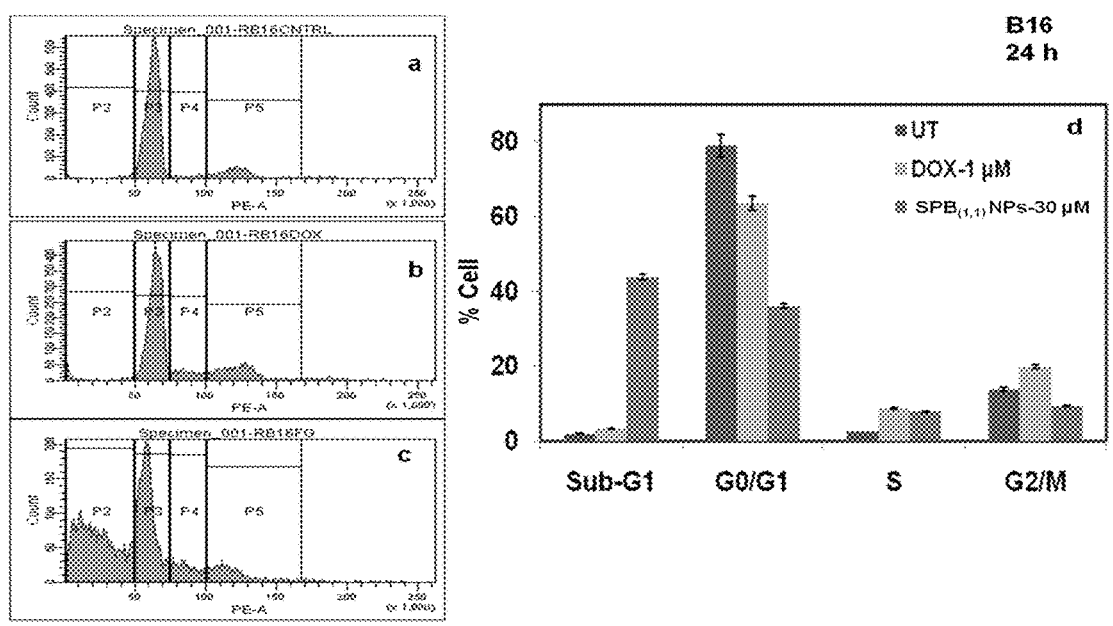
Fig.9.a-d

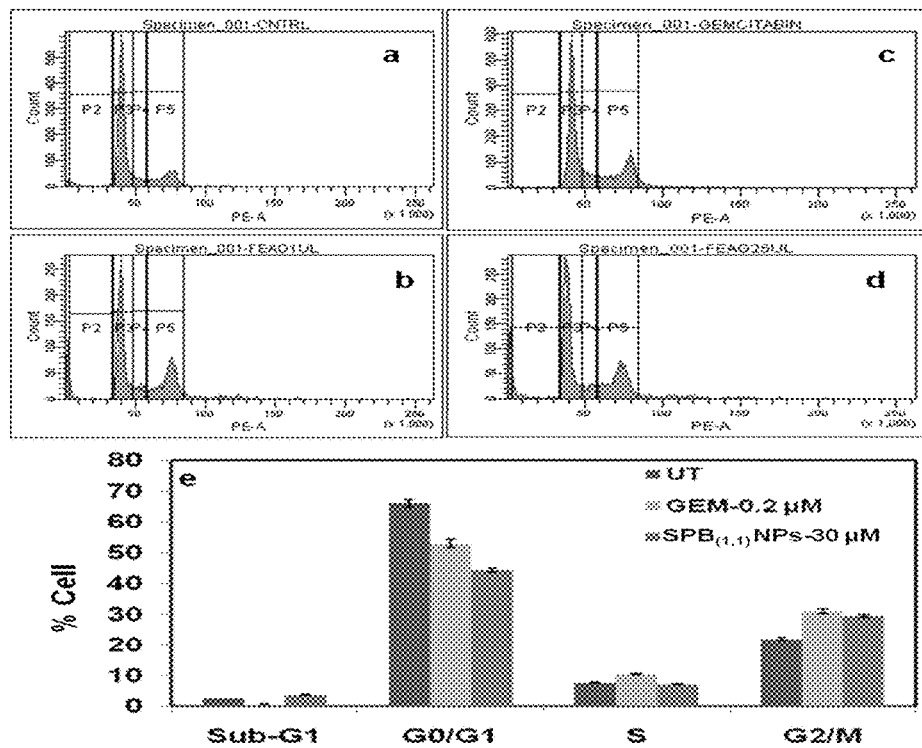

Fig.12 40X — Analysis of nuclear damage by Hoechest staining

Fig.14.a-d

Fig. 17    Agar disc diffusion method

B-Blank
K-Kanamycin
S-Streptomycin
Z-Zentamycin
P-Pencillin
N-SPB$_{(1,1)}$ NPs(30µM)

Colony counting method in E. coli and Bacillus subtilis (Gram +ve)

Control      Streptomycin         SPB$_{(1,1)}$ NPs (30 μM)
             (5 μg/ml)

Inhibition of soil bacterial growth by SPB$_{(1,1)}$ NPs

BIOCAMPATIBLE POLYMER COATED SILVER PRUSSIAN BLUE NANOPARTICLES (SPB-NPS: AG$_3$[FE(CN)$_6$])

CROSS-REFERENCE TO RELATED APPLICATION

This application claims priority to India Provisional Application No. 0502/DEL/2015, entitled, "Biocompatible Polymer Coated Silver Prussian Blue Nanoparticles (SPB-NPS: Ag$_3$[Fe(CN)$_6$])" filed Feb. 23, 2015, and benefit of the filing date of this prior application is hereby claimed. The prior application is hereby incorporated by reference in its entirety.

FIELD OF THE INVENTION

The present invention relates to biocompatible polymer coated silver prussian blue nanoparticles (SPB-NPS: Ag$_3$[Fe(CN)$_6$]). Particularly, the present invention relates to an improved method for the synthesis of poly(N-vinyl-2-pyrrolidone) (PVP)-stabilized silver hexacyanoferrate nanoparticles (silver Prussian blue analogue: Ag$_3$[Fe(CN)$_6$] abbreviated as SPB-NPs) where polymer acts as stabilizing or capping agent. The as-synthesized nanoparticles (SPB-NPs) have been thoroughly characterized by several analytical tools. The SPB-NPs are highly stable for more than two weeks towards different physiological buffers or solutions with different pH (pH=6, ~7.4 & ~8). These nanoparticles (SPB-NPs) exhibit biocompatibility towards various normal cells (HUVEC, CHO, & ECV304) but show significant inhibition of proliferation of different cancer cells in vitro and tumor growth in C57/BL6/J mice model (aggressive murine melanoma cancer model: B16F10). Additionally, the SPB-NPs show excellent antibacterial activity towards gram-negative (*E. coli*) and gram-positive (*B. subtilis*) bacteria. Consider all results together; these biocompatible SPB-NPs would be potentially useful for the development towards alternative anti-cancer agent as well as anti-bacterial agent in near future.

BACKGROUND AND PRIOR ART OF THE INVENTION

Since the last decade, metal nanoparticles have been considerably explored for the treatment of several diseases such as cancer, cardiovascular related diseases, diabetes, Parkinson's, arthritis, HIV, hepatitis, tuberculosis, Alzheimer's, cirrhosis etc due to their unique fundamental physical and chemical properties (Alivisatos, P. et al, Nat. Biotechnol. 2004; 22: 47-52; Boisselier, E. et al. Chem. Soc. Rev. 2009; 38: 1759-1782; Gao, X. et al. Nat. Biotechnol. 2004; 22: 969-976; Kumar, A. et al. Nat. Mater. 2008; 7: 236-241; Mulder, W. J. M. et al. Arterioscl. Throm. Vas. 2008; 28: 801-802; Patra, C. R. et al. Adv. Mater. 2008; 20: 753-756; Patra, C. R. et al. Cancer research, 2008; 68: 1970-1978; Patra, C. R. et al. Nano Lett. 2011; 11: 4932-4938; Shankar, S. S. et al. Nat. Mater. 2004; 3: 482-488; Sung, H. W. et al. Nanomedicine-Uk, 2011; 6: 1297-1300; Wei, P. F. et al. Biomaterials, 2014; 35: 899-907). Recently scientists have discovered new classes of nanoparticles i.e. metal complex nanoparticles such as Prussian blue nanoparticles (PBNPs) and its analogs (Collins, A. M. et al. Nanoscale, 2010; 2: 2370-2372; De la Escosura, A. et al. Chem. Comm. 2008; 1542-1544; Dominguez-Vera, J. M. et al. Inorganic chemistry, 2003; 42: 6983-6985; Dumont, M. F. et al. Int. J. Nanomedicine, 2014; 9: 2581-2595; Fiorito, P. A. et al. Chem. Comm. 2005; 366-368; Fu, G. et al. Chem. Comm. 2012; 48: 11567-11569; Hornok, V. et al. J. Colloid Interface Sci. 2007; 309: 176-182; Hu, M. et al. Angew Chem. Int. Ed. Engl. 2012; 51: 984-988; Uemura, T. et al. J. Am. Chem. Soc. 2003; 125: 7814-7815; Wang, H. et al. J. Hazard. Mater. 2011. 191, 163-169; Ye, S. et al. Chem. Comm. 2011; 47: 6831-6833) (Kawamoto et al. EP2116511 A1, 2009; Kawamoto et al. US7678188 B2, 2010; Kawamoto et al. U.S. Pat. No. 8,349,221 B2, 2013). Incorporation of metals in the co-ordination complexes change their properties that could be useful for chelating agent for heavy metal toxicity, coating medium, drug delivery vehicles, MRI substance, luminescent materials, sensors etc. (Dumont, M. F. et al. Int. J. Nanomedicine, 2014; 9: 2581-2595; Fiorito, P. A. et al. Chem. Comm. 2005; 366-368; Fu, G. et al. Chem. Comm. 2012; 48: 11567-11569; Ye, S. et al. Chem. Comm. 2011; 47: 6831-6833). Prussian blue complex has gained huge interests to remove the heavy metals and radioactive elements due to its chelating property (Stevens, W. et al. Therapy and toxicology, 1974; 10: 1-22; Thompson, D. F. et al. The Annals of pharmacotherapy, 2004; 38: 1509-1514). Because of the biocompatibility nature, PBNPs have been utilized for several theranostics applications like drug delivery, MRI imaging etc. (Jing, L. et al. Biomaterials, 2014; 35: 5814-5821; Lian, H. Y. et al. Chem. Comm. 2012; 48: 5151-5153; Schleich, N. et al. Int. J Pharm. 2013; 447: 94-101). However, potential biomedical applications of Prussian blue analogs have not been extensively explored for cancer therapeutics and antibacterial activity study. In this context, we have designed and developed polymer stabilized silver Prussian blue analogue, Ag$_3$[Fe(CN)$_6$] that exhibit itself as potential anticancer as well as anti-bacterial agent without external source of anti-cancer drugs or antibiotics. The present invention discloses an improved synthesis of highly stable silver Prussian blue nanoparticles (SPB-NPs) and its therapeutic applications towards anticancer and antibacterial activities. Additionally, the detailed mechanistic studies for the anticancer and antibacterial activities have been discussed. The present invention described the simple improved method for the synthesis biocompatible SPB-NPs would be potentially useful for the development towards alternative anti-cancer agent as well as anti-bacterial agent in near future.

SUMMARY OF THE INVENTION

The present disclosure relates to biocompatible polymer coated silver prussian blue nanoparticles (SPB-NPS: Ag$_3$[Fe(CN)$_6$]). Particularly, the present invention relates to an improved method for the synthesis of poly(N-vinyl-2-pyrrolidone) (PVP)-stabilized silver hexacyanoferrate nanoparticles (silver Prussian blue analogue: Ag$_3$[Fe(CN)$_6$] abbreviated as SPB-NPs) where polymer acts as stabilizing or capping agent. The present disclosure also shows the effective antibacterial activity in gram-negative (*E. coli*) as well as gram-positive (*B. subtilis*) bacteria at low concentration of silver (~20-30 μM) and its plausible mechanism of actions. The present disclosure further shows in vitro & in vivo anticancer activity of SPB-NPs itself and probable mechanism. The present disclosure provides a description of designing and developing an improved method for the synthesis of highly stable, biocompatible SPB-NPs that could be utilized as the alternative low cost anti-cancer drug & anti-bacterial agent.

Accordingly the present invention discloses an improved method for the synthesis of silver analogues of Prussian blue nanoparticles (SPB-NPs) using polymer as a stabilizing agent. The invention also discloses that these nanoparticles are highly crystalline & spherical with size 5-40 nm in size. Additionally, the present invention also discloses the synthesis of SPB-NPs by changing the volume ratio of $10^{-3}$ (M) $AgNO_3$ solution and $10^{-3}$ (M) $K_3Fe(CN)_6$ from 1:1 to 1:2 via 2:1 ($SPB_{(1,1)}$, $SPB_{(2,1)}$ and $SPB_{(1,2)}$). In an preferred embodiment of the present invention, wherein SPB-NPs show high stability, one of the important criteria for drug delivery, towards various biological buffers/solutions with different pH.

In another embodiment of the present invention, wherein the SPB-NPs show high biocompatibility towards various normal cells (human umbilical vein endothelial cells: HUVEC; Chinese hamster ovarian cells: and ECV-304) up to very high concentration of silver.

In still another embodiment of the present invention, wherein the SPB-NPs exhibit profound antibacterial activity in gram-negative (*E. coli*) as well as gram-positive (*B. subtilis*) bacteria at low concentration of silver.

In yet another embodiment of the present invention, wherein the detailed mechanism behind the antibacterial actions has been explored. Catalase, super oxide dismutase (SOD) levels decreased in SBP-NPs treated bacteria and stress proteins are upregulated and lipid peroxidation (LPO) level also increased suggesting the probable mechanism of anti-bacterial activity.

In another embodiment of the present invention, wherein SPB-NPs show excellent anticancer property towards different cancer cells (lung, breast, melanoma and ovarian) at very low doses. The investigation of detailed mechanism for the anticancer activity shows involvement of caspase mediated (apoptosis) and p53 regulated pathways.

In still another preferred embodiment of the present invention, wherein inhibition of migration of cancer cells in presence of SPB-NPs in wound healing scratching assay indicates the prevention of migration of cancer cells from one organ to another (metastasis).

In an embodiment of the present invention, wherein the evaluation of in vivo anticancer activity of SPB-NPs in B16F10 aggressive murine melanoma tumor model. SPB-NPs treated C57/BL6/J mice show excellent tumor regression. Further detailed mechanistic study has been investigated and found the involvement of caspase mediated (apoptosis) and p53 regulated pathways and down regulation of epidermal growth factor receptor (EGFR), Stat-3 and Bcl-2.

In yet another embodiment of the present invention, wherein the SPB-NPs could be administered through several routes such as subcutaneous, intravenous (IV), intramuscular (IM) & intraperitonial (IP).

BRIEF DESCRIPTION OF THE DRAWINGS

FIG. 6: Stability studies of as synthesized $SPB_{(1,1)}$NPs showed the long term stability of as synthesized nanoparticles in various physiological buffers and saline solutions.

FIG. 7.*a-e*: The toxicity study of $SPB_{(1,1)}$NPs in different normal cells (CHO, ECV-304 & HUVEC) by MTT assay in 24 & 48 hours. Numerical values indicate the concentration of silver in μM. The MTT result shows the biocompatible nature of $SPB_{(1,1)}$NPs up to 30 μM doses in different cells.

FIG. 8.*a-d*: In vitro anticancer study of $SPB_{(1,1)}$NPs in different cancer cells (SKOV3, MCF7, A549 and B16F10) by MTT assay for 24 hours in a dose dependent manner. Numerical values indicate the concentration of silver in μM. Results show the high anticancer activity of $SPB_{(1,1)}$NPs in all these cancer cells.

FIG. 9.*a-d*: FACS analysis of untreated, $SPB_{(1,1)}$NPs and DOX (1 μM) treated B16F10 cancer cells show sub-G1 and S-phase arrest.

FIG. 10.*a-e*: FACS analysis of untreated, $SPB_{(1,1)}$NPs and GEM (0.2 μM) treated B16F10 cancer cells show G2/M phase arrest.

DETAILED DESCRIPTION OF THE INVENTION

Figure 1:
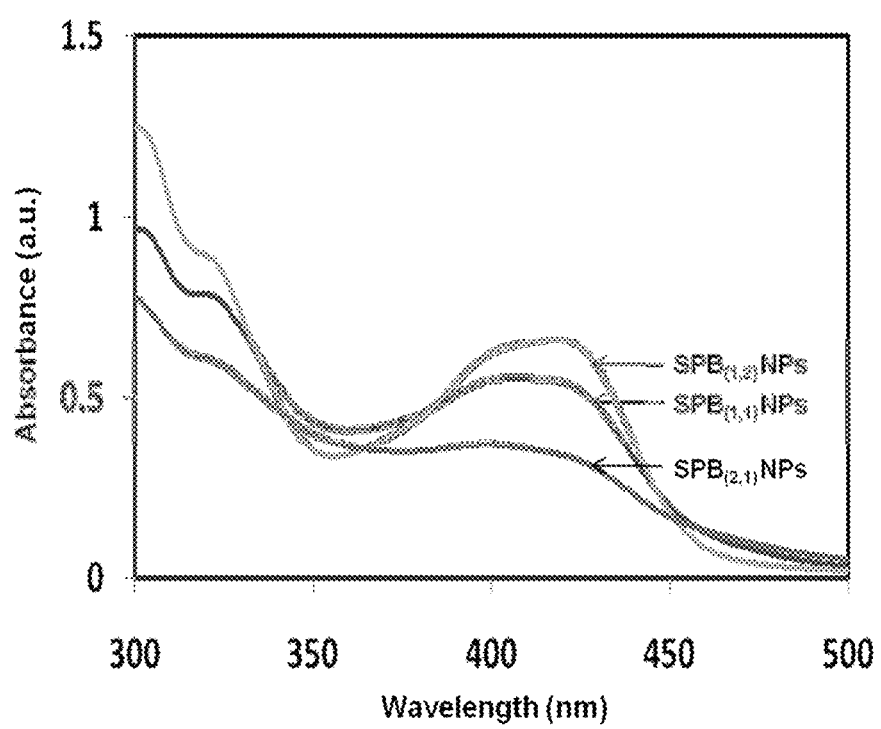
FIG. 1: UV-visible spectrum of the as synthesized SPB-NPs synthesized by the interaction of $K_3Fe(CN)_6$ and $AgNO_3$ in presence of PVP as a stabilizing agent. Comparative studies of UV absorbance of $SPB_{(1,1)}$, $SPB_{(2,1)}$ and $SPB_{(1,2)}$ NPs have been checked at 24 hours, where subscript values indicate the volume ratio of $K_3Fe(CN)_6$ and $AgNO_3$.

The present invention provides biocompatible polymer coated silver prussian blue nanoparticles (SPB-NPS:$Ag_3[Fe(CN)_6]$) and an improved method for the synthesis of poly(N-vinyl-2-pyrrolidone) (PVP)-stabilized silver hexacyanoferrate nanoparticles (silver prussian blue analogue: $Ag_3[Fe(CN)_6]$ abbreviated as SPB-NPs) by the interaction of $AgNO_3$ solution and $K_3Fe(CN)_6$ solution. Here, polymer has been used as stabilizing or capping agent during the synthesis of SPB-NPs. The nanoparticles have been synthesized by changing the volume ratio of $10^{-3}$ (M) $AgNO_3$ solution and $10^{-3}$ (M) $K_3Fe(CN)_6$ from 1:1 to 1:2 via 2:1 where the nanoparticles are abbreviated as $SPB_{(1,1)}$ NPs, $SPB_{(2,1)}$ NPs and $SPB_{(1,2)}$ NPs. The silver analogs with other metals could be prepared by replacing the $Fe^{III}$ with $M^{III}$=V, Cr, Mn, Co, Ru, Gd, Eu, Sm, Tb etc. in $[K_3Fe^{III}(CN)_6]$. All nanoparticles have been characterized thoroughly by several analytical tools. Based on the size, stability, monodispersity, we have selected $SPB_{(1,1)}$ NPs for further in vitro as well as in vivo studies. The $SPB_{(1,1)}$-NPs are highly stable for more than two weeks towards different physiological buffers or solutions with different pH (pH=6, −7.4 & −8). These nanoparticles ($SPB_{(1,1)}$-NPs) exhibit biocompatibility towards various normal cells (HUVEC, CHO, & ECV304) but show significant inhibition of proliferation to several cancer cells in vitro and tumor growth in C57/BL6/J mice model (aggressive murine melanoma cancer model: B16F10). Additionally, the $SPB_{(1,1)}$NPs show excellent antibacterial activity towards gram-negative (*E. coli*) and gram-positive (*B. subtilis*) bacteria. The whole experimental study for this invention has been classified into several parts such as (i) synthesis of PVP stabilized SPB-NPs nanoparticles, (ii) detailed characterizations of the as synthesized SPB-NPs, (iii) in vitro and in vivo anticancer studies of $SPB_{(1,1)}$-NPs, (iv) probable mechanism and (v) antibacterial activities of $SPB_{(1,1)}$ NPs and their detailed mechanism studies. Consider all results together; these biocompatible SPB-NPs would be potentially useful for the development towards alternative anti-cancer agent as well as anti-bacterial agent in near future.

The following examples are provided to illustrate the present invention and should not be constructed as limiting the scope of the invention described in the claims.

EXAMPLES

Example-1: Materials

Silver nitrate ($AgNO_3$), potassium ferricyanide [$K_3Fe(CN)_6$], Poly Vinyl Pyrrolidone (PVP), MTT reagent [3-(4,5-dimethylthiazol-2-yl)-2,5-diphenyltetrazolium bromide)], ribonuclease (RNase), propidium iodide (PI), doxorubicin (Dox), sodium dodecyl sulphate (SDS), RIPA buffer, protease inhibitor cocktail, tris-Hcl, glycine and methanol were purchased from Sigma Aldrich Chemicals, St. Louis, Mo., USA and used without further purification. Cell lines: Chinese hamster ovary cell line (CHO), mouse melanoma cancer (B16F10), human lung cancer (A549). Human breast cancer (MCF-7), human umbilical vein endothelial cells (HUVEC), human ovarian cancer cells (SKOV3) cells and ECV-304 cells have been purchased from ATCC, USA. ECV-304 (M- Cells) cells were a kind gift from Dr. V. Shah, Chair, Gastroenterology and Hepatology Department, Mayo Clinic, Rochester, Minn., USA. Stock solution preparation: Initially, $10^{-3}$ (M) $AgNO_3$ solution and $10^{-3}$ M $K_3Fe(CN)_6$ stock solution was prepared in sterile Millipore water for the synthesis of silver Prussian blue nanoparticles (SPB-NPs). 1% PVP was prepared by dissolving 1 gm PVP in ethyl alcohol.

Example-2: Synthesis of Silver Prussian Blue Nanoparticles Analogue (SPB-NPs)

The reaction was initiated by the addition of 50 ml of $10^{-3}$ (M) $K_3Fe(CN)_6$ and 50 ml of $10^{-3}$ (M) $AgNO_3$ under constant stirring. The yellow colored $K_3Fe(CN)_6$ was became little intense after the addition of $AgNO_3$. The reaction was stabilized with the addition of 400 μL of 1% PVP and kept for overnight stirring. The nanoparticles have been synthesized by changing the volume ratio of $10^{-3}$ (M) $AgNO_3$ solution and $10^{-3}$ (M) $K_3Fe(CN)_6$ from 1:1 to 1:2 via 2:1 where the nanoparticles are abbreviated as $SPB_{(1,1)}$ NPs, $SPB_{(2,1)}$ NPs and $SPB_{(1,2)}$ NPs. Also, we have varied the amount of PVP polymer (4 μL, 40 μL, 400 μL and 4 mL) to check the optimized reaction sets for SPB-NPs. The brownish yellow colored pellet was obtained after centrifugation at 17,700 rpm for 45 minutes at 15° C. This concentrated brownish yellow pellet was further used for all the characterizations and biological studies. All nanoparticles have been characterized thoroughly by several analytical tools. The experimental detailed for the synthesis of $SPB_{(1,1)}$ NPs, $SPB_{(2,1)}$ NPs and $SPB_{(1,2)}$ NPs and their size and charge are provided in Table-1. Based on the size, stability, monodispersity, we have selected $SPB_{(1,1)}$ NPs for further in vitro as well as in vivo studies.

Example-3: Scheme-1

TABLE 1

Synthesis, conditions and characterization of the as synthesized SPB-NPs synthesized by the interaction of K3Fe(CN)6 and AgNO3 in presence of PVP as a stabilizing agent.

| S. No | AgNO3 | K3Fe(CN)6 | Ratio | Added PVP | DLS Size and charge | TEM size | TEM shape | UV (wave length) |
|---|---|---|---|---|---|---|---|---|
| 1) | 5 ml | 5 ml | 1:1 | 40 μl | 43 nm and −19.1 mV | 15-22 nm | Spherical and rod | 405 nm |

TABLE 1-continued

Synthesis, conditions and characterization of the as synthesized SPB-NPs synthesized by the interaction of K3Fe(CN)6 and AgNO3 in presence of PVP as a stabilizing agent.

| S. No | $AgNO_3$ | $K_3Fe(CN)_6$ | Ratio | Added PVP | DLS Size and charge | TEM size | TEM shape | UV (wave length) |
|---|---|---|---|---|---|---|---|---|
| 2) | 6.66 ml | 3.33 ml | 2:1 | 40 μl | 114.3 nm and −25.8 mV | 20-33 nm | Spherical | 401 nm |
| 3) | 3.33 ml | 6.66 ml | 1:2 | 40 μl | 200.1 nm and −32.8 mV | 5-20 nm | Spherical and rod | 416 nm |
| 4) | 5 ml | 5 ml | 1:1 | 4 μl | 2312 nm and −28.3 mV | 15-25 nm | Spherical | 402 nm |
| 5) | 5 ml | 5 ml | 1:1 | 4000 μl | 181.7 nm and −8.97 mV | 14-23 nm | Spherical | 410 nm |
| 6) | 5 ml | 5 ml | 1:1 | 400 μl | 87.33 nm and −25.6 mV | 10-25 nm | Spherical | 412 nm |

Figure 21:
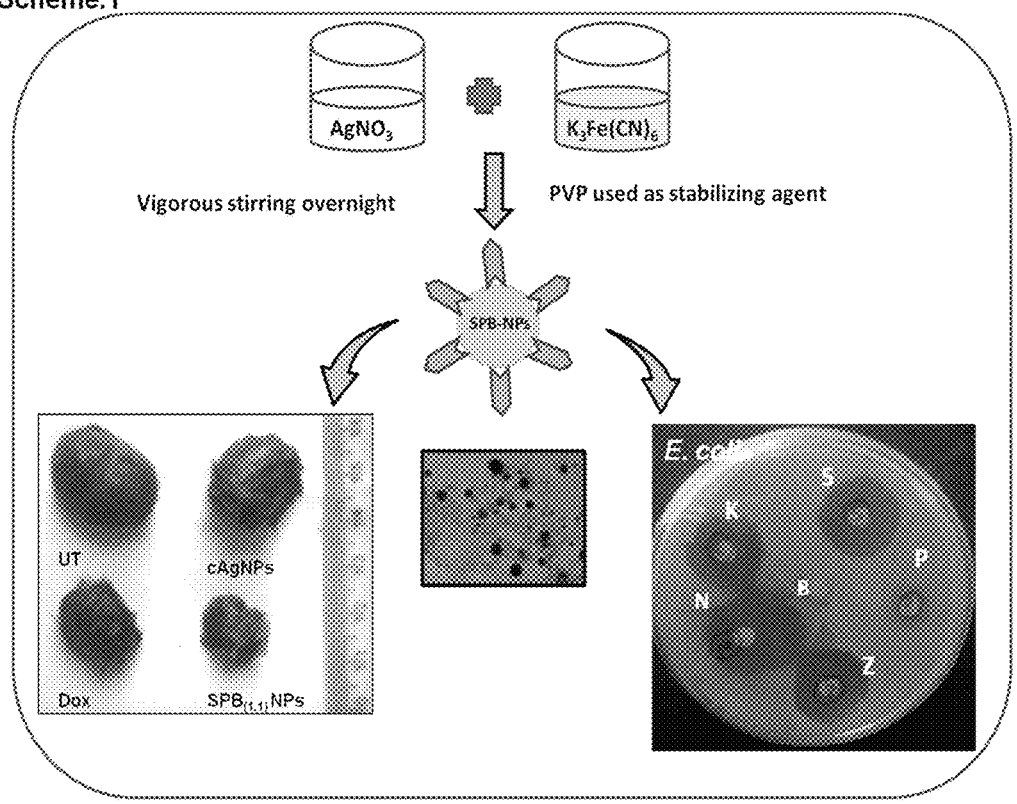
FIG. 21: Scheme-1, showing overall scheme of synthesis, characterization and anti-cancer and anti-bacterial effect of the as synthesized $SPB_{(1,1)}$-NPs synthesized by the interaction of $K_3Fe(CN)_6$ and $AgNO_3$ in presence of PVP as a stabilizing agent.

This example-3, as shown in Scheme-1 in FIG. 21, describes the overall synthesis, characterization and biological activities of $SPB_{1,1}$-NPs. The synthesis of poly(N-vinyl-2-pyrrolidone) (PVP)-stabilized silver hexacyanoferrate nanoparticles (silver Prussian blue analogue: $Ag_3[Fe(CN)_6]$ abbreviated as SPB-NPs) by the interaction of $AgNO_3$ solution and $K_3Fe(CN)_6$ solution in 1:1 volume ratio. The whole experimental study for this invention has been classified into several parts such as (i) synthesis of PVP stabilized $SPB_{1,1}$-NPs nanoparticles, (ii) detailed characterizations of the as synthesized $SPB_{1,1}$-NPs, (iii) in vitro and in vivo anticancer studies of $SPB_{(1,1)}$-NPs, (iv) probable mechanism and (v) antibacterial activities of $SPB_{(1,1)}$ NPs and their detailed mechanistic studies. Consider all results together; these biocompatible SPB-NPs would be potentially useful for the development towards alternative anticancer agent as well as anti-bacterial agent in near future (Scheme-1).

Example-4: UV Visible Spectroscopy

This example illustrates the UV visible characterization of silver analog Prussian blue nanoparticles (SPB-NPs). The three SPB-NPs have been synthesized by changing the volume ratio of $10^{-3}$ (M) $AgNO_3$ solution and $10^{-3}$ (M) $K_3Fe(CN)_6$ from 1:1 to 2:1 via 2:1 where the nanoparticles are abbreviated as $SPB_{(1,1)}$ NPs, $SPB_{(2,1)}$ NPs and $SPB_{(1,2)}$ NPs. All the nanomaterials show light yellow coloration and hence their absorbance have been monitored by using UV-Vis spectroscopy (JASCO dual-beam spectrophotometer (Model V-570) in a quartz cuvette from 800 to 200 nm with a resolution of 1 nm. The as synthesized SPB-NPs were characterized by different physico-chemical techniques. UV-visible spectra indicate the formation of SPB-NPs. It showed the absorption peak at $\lambda_{max}$=410-430 nm reflects the yellow color of the reaction mixture (FIG. 1).

Example-5: X-Ray Diffraction (XRD) Spectroscopy

Figure 2:
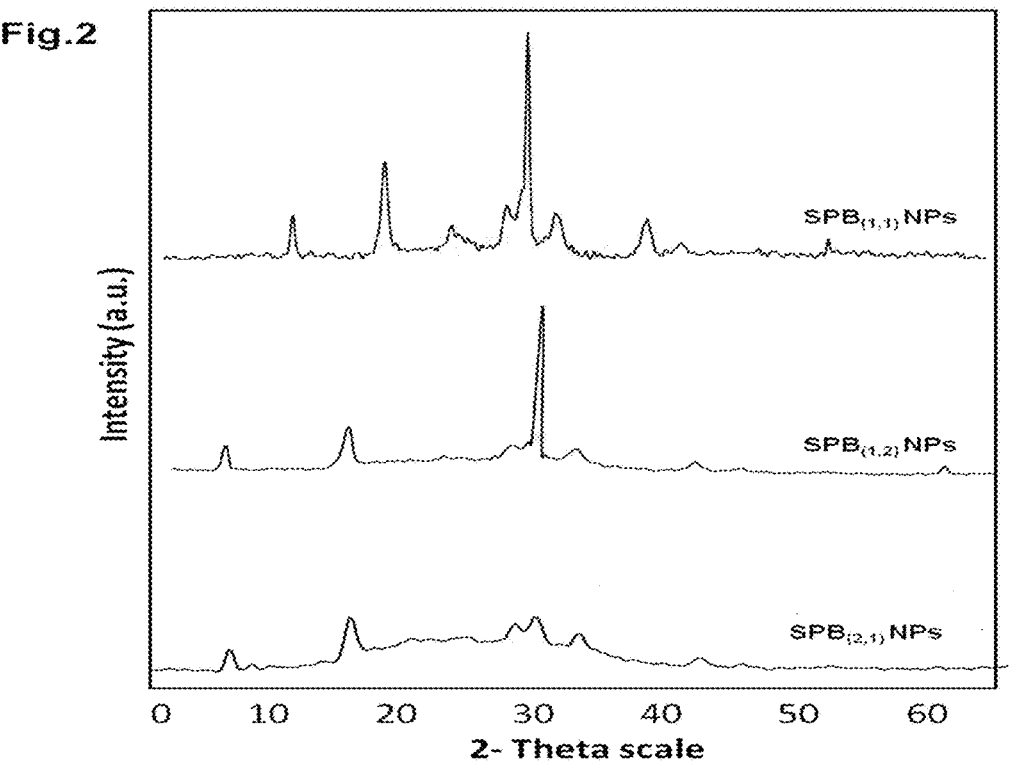
FIG. 2: XRD pattern of $SPB_{(1,1)}$, $SPB_{(2,1)}$ and $SPB_{(1,2)}$ NPs show the FCC crystalline nature of the as synthesized $SPB_{(1,1)}$NPs.

This example illustrates the X-ray diffraction (XRD) spectroscopic characterization of silver analog Prussian blue nanoparticles (SPB-NPs). The three SPB-NPs have been synthesized by changing the volume ratio of $10^{-3}$ (M) $AgNO_3$ solution and $10^{-3}$ (M) $K_3Fe(CN)_6$ from 1:1 to 1:2 via 2:1 where the nanoparticles are abbreviated as $SPB_{(1,1)}$ NPs, $SPB_{(2,1)}$ NPs and $SPB_{(1,2)}$ NPs. This instrument is used to determine the crystalline structure of SPB-NPs. XRD works on the principle of BRAGG'S LAW. The brownish-yellow colored pellet of SPB-NPs was obtained by centrifugation at a 17,700 rpm at 15° C. for 45 mins in Thermo scientific, Sorvall-WX ultra 100. We layered the pellet on the glass slide and submitted for XRD analysis. The instrument model used for X-ray diffraction (XRD) analysis was Bruker AXS D8 Advance Powder X-ray diffractometer (using CuKαλ=1.5406 Å radiation). XRD data indicates the FCC crystalline nature of the as synthesized $SPB_{(1,1)}$, $SPB_{(2,1)}$ and $SPB_{(1,2)}$ NPs (FIG. 2).

Example-6: Transmission Electron Microscopy (TEM) and Dynamic Light Scattering (DLS)

Figure 3:
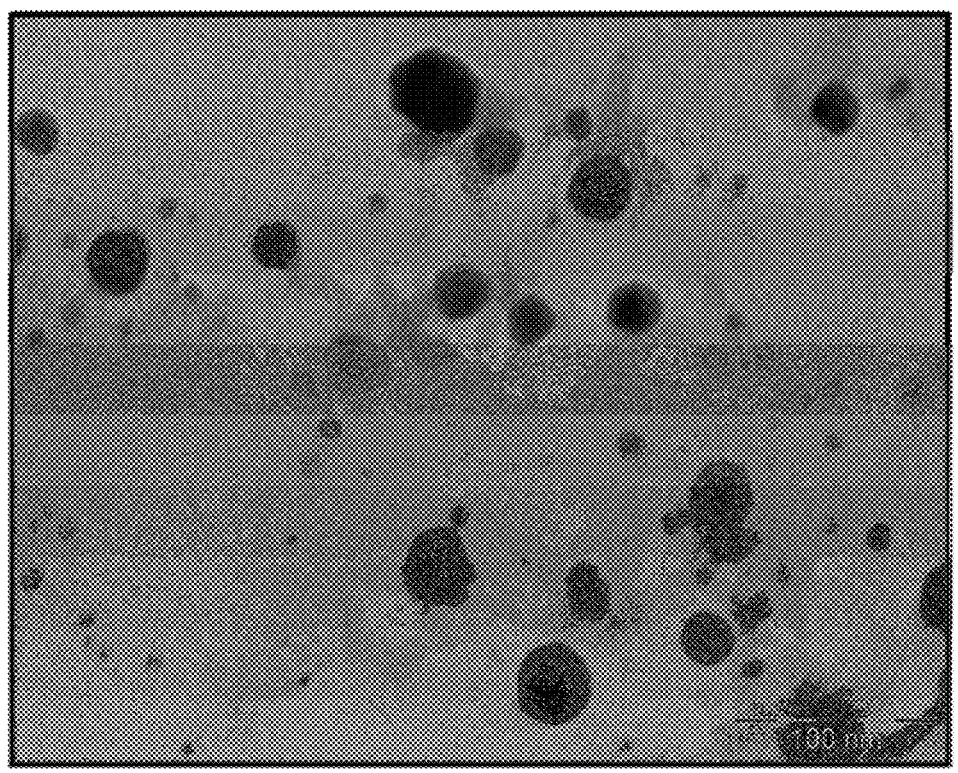
FIG. 3: TEM images of as synthesized $SPB_{(1,1)}$NPs show spherical shape and 6-20 nm size.
Figure 4:
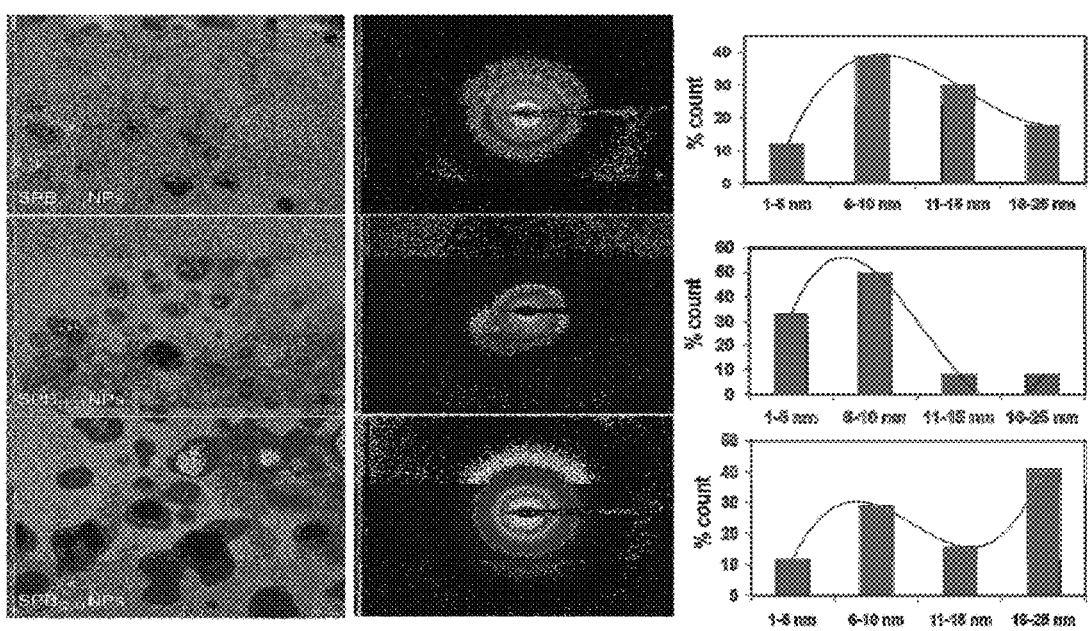
FIG. 4: Comparative TEM images, SAED pattern and size distribution of $SPB_{(1,1)}$, $SPB_{(2,1)}$ and $SPB_{(1,2)}$ NPs.

This example illustrates the Transmission electron microscopy (TEM) characterization of silver analog Prussian blue nanoparticles (SPB-NPs). TEM is used to analyze the morphology of SPB-NPs. The shape and morphology of nanoparticles were obtained from TEM [FEI Tecnai F12 (Philips Electron Optics, Holland)] instrument operated at 100 keV. Selected area electron diffraction (SAED) patterns were also taken using this instrument. TEM study reveals that the as synthesized $SPB_{(1,1)}$, $SPB_{(2,1)}$ and $SPB_{(1,2)}$ NPs are spherical in nature and almost monodispersed in nature. The size of $SPB_{(1,1)}$, $SPB_{(2,1)}$ and $SPB_{(1,2)}$ NPs are 6-22 nm, 7-33 nm and 6-20 nm respectively (Table 1, FIG. 3-4). The size and charge of SPB-NPs is obtained using DLS. We submitted diluted pellet for DLS analysis the Size and zeta potential (ξ) of SPB-NPs were calculated by DLS analyzer (HORIBA SZ-100) using quartz cuvette. There is no sign of aggregation. Also, from DLS, the size obtained is (43±2.5) nm and the zeta potential (ξ) value is −19.1 mV reflects high colloidal stability of the as synthesized $SPB_{(1,1)}$NPs (Table 1). So, by checking the color, stability, size $SPB_{(1,1)}$NPs has been considered as the optimized set for all the biological experiments.

Example-7: Fourier Transformed Infrared (FTIR) Spectroscopy

Figure 5:
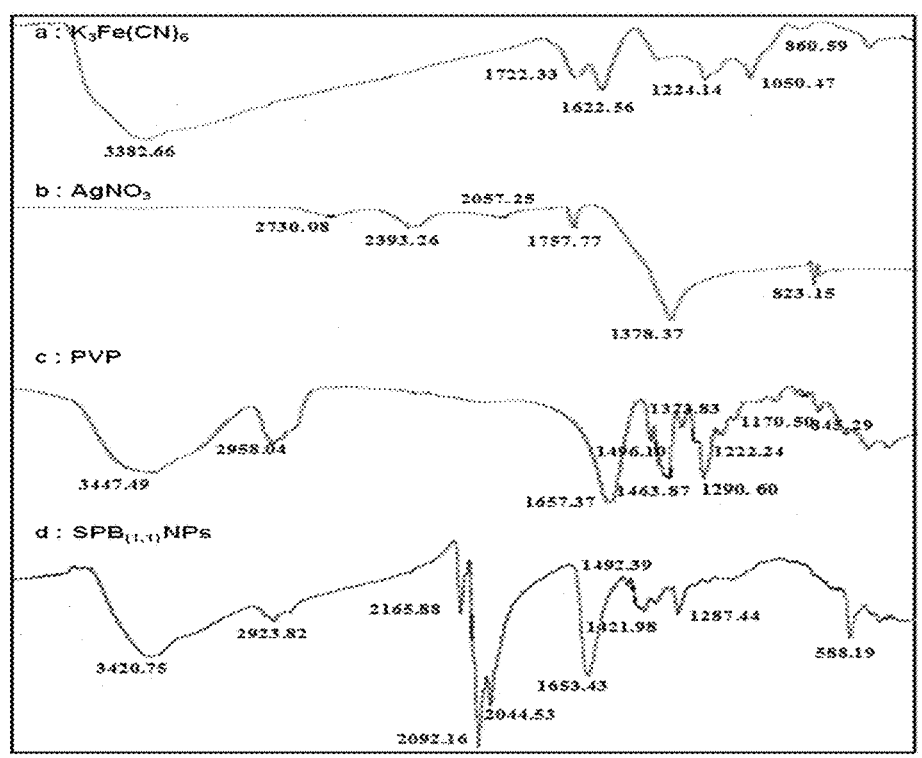
FIG. 5: FTIR spectrum of $K_3Fe(CN)_6$, PVP, $AgNO_3$ and $SPB_{(1,1)}$NPs.

This example illustrates the Fourier transformed infrared (FTIR) spectroscopic characterization of silver analog Prussian blue nanoparticles ($SPB_{(1,1)}$-NPs) along with $K_3Fe(CN)_6$, $AgNO_3$ and PVP. This instrument is used to examine the functional groups of SPB-NPs. We have coated the pellet on the glass slide and submitted for FTIR analysis. FTIR Model used for analyzing is thermo Nicolet Nexus 670 spectrometer in the diffuse reflectance mode at a resolution of 400 to 4000 cm$^{-1}$ in KBr pellets. FTIR study clearly shows that the peaks observed in SPB$_{(1,1)}$NPs is a combined peaks of K$_3$Fe(CN)$_6$, PVP, AgNO$_3$ (FIG. 5).

Example-8: Stability Studies of SPB$_{(1,1)}$-NPs

This example illustrates the stability studies of silver analog Prussian blue nanoparticles (SPB$_{(1,1)}$-NPs). The synthesis of SPB$_{(1,1)}$-NPs was done as explained in example-2. The as-synthesized SPB$_{(1,1)}$-NPs has been incubated with various pH solutions (pH=6, -7.4 & -8), and saline solution for 2 weeks. The SPB$_{(1,1)}$-NPs are highly stable for more than two weeks towards different physiological buffers or solutions with different pH (pH=6, -7.4 & -8) and salt solution. (FIG. 6)

Example-9: Inductively Coupled Plasma Optical Emission Spectrometry (ICP-OES)

To determine the silver, iron and potassium concentrations in SPB-NPs and cAgNPs pellets an inductively coupled plasma optical emission spectrometer (ICP-OES, IRIS intrepid II XDL, ThermoJarrel Ash) was used. From, ICP-OES study the concentrations of silver and iron has been determined and found that the metal content present in SPB$_{(1,1)}$NPs are Iron (Fe)=1.5 ppm; Silver (Ag)=4.05 ppm and Potassium (K)=0.01 ppm. So, potassium concentration is almost negligible and the structure can be predicted as Ag$_3$[Fe(CN)$_6$].

Example-10: Cell Culture and In Vitro Toxicity Studies (MTT)

This example illustrates the cytotoxicity of silver analog Prussian blue nanoparticles (SPB$_{(1,1)}$-NPs) in normal cells. The synthesis of SPB$_{(1,1)}$-NPs was done as explained in example-2. Chinese hamster ovary cell line (CHO), and ECV-304 cells were cultured in DMEM supplemented with 10% fetal bovine serum (FBS), 5% L-glutamine, and 1% antibiotics (penicillin, streptomycin purchased from Sigma-Aldrich) in a humidified 5% CO$_2$ incubator at 37° C. Human umbilical vein endothelial cells (HUVEC) were cultured in EBM complete media at 37° C. incubator with 5% CO$_2$ according to our published literature. The colorimetric MTT assay is for the measurement of cytotoxicity of the compound to be screened. In this method the yellow colored (3-(4, 5-dimethylthiazol-2-yl))-2, 5-diphenyl tetrazolium bromide dye turns into formazan crystals by the action of succinate dehydrogenase enzyme from mitochondria. Chinese hamster ovary cell line (CHO), HUVEC and ECV-304 cell were seeded in 96 well plates (10,000 cells/well) and incubated for 24 hours. The silver Prussian blue nanoparticles (SPB$_{(1,1)}$NPs) were treated to the cultured cells in a dose dependent manner and again incubated for further 24/48 hours. The old media was removed and 100 µl of MTT reagent (5 mg/ml) was added to each well. The cells were solubilized by the DMSO-Methanol (1:1 ratio). The absorbance of the purple color developed was measured in micro plate reader (ELx 800 MS) at 570 nm. All the experiments were carried out in triplicate and the results are expressed as normalized viability. To determine the toxicity nature of the SPB$_{(1,1)}$NPs, we screened in HUVEC, CHO, ECV-304-cell lines. The MTT results showed that these materials are biocompatible in CHO cell line up to 90 µM concentration. (FIG. 7.a-b). The biocompatibility nature of these materials has been also existed in HUVEC and ECV-304-cells up to 30 µM concentration (FIG. 7.c-e).

Example-11: In Vitro Anticancer Activity (MTT Assay)

This example illustrates the anticancer activity of silver analog Prussian blue nanoparticles (SPB$_{(1,1)}$-NPs) in various human and mouse cancer cells. The synthesis of SPB$_{(1,1)}$-NPs was done as explained in example-2. Mouse melanoma cancer (B16F10), human lung cancer (A549). Human breast cancer (MCF-7), human ovarian metastatic cancer cells (SKOV3) cells were cultured in DMEM supplemented with 10% fetal bovine serum (FBS), 5% L-glutamine, and 1% antibiotics (penicillin, streptomycin purchased from Sigma-Aldrich) in a humidified 5% CO$_2$ incubator at 37° C. All these cells were seeded in 96 well plates (10,000 cells/well) and incubated for 24 hours. The silver Prussian blue nanoparticles (SPB$_{(1,1)}$NPs) were treated to the cultured cells in a dose dependent manner and again incubated for further 48 hours. The old media was removed and 100 µl of MTT reagent (5 mg/ml) was added to each well. The cells were solubilized by the DMSO-Methanol (1:1 ratio). The absorbance of the purple color developed was measured in micro plate reader (ELx 800 MS) at 570 nm. SPB$_{(1,1)}$NPs showed the cytotoxic effect on the human ovarian cancer (SKOV3) cells, human lung cancer cells (A549), human breast cancer cells (MCF7) and mouse melanoma cells (B16) when treated with a dose dependent manner. 30 µM concentrations were found to be much cytotoxic after 48 hours (FIG. 8.a-d). Recently we have discussed about the cell specific action of biosynthesized silver nanoparticles, which gives an idea about the anticancer activity of these materials. The release of the silver ions from the silver nanoparticles would be the possible reason for the cytotoxicity in cancer cell line. More over the pathways that are carried in the normal cell and the cancer cell is also different. So based on the interaction of these nanoparticles with biomolecules may give the different action on different cell line.

Example-12: Cell Cycle Assay by FACS (Fluorescence Activated Cell Sorting)

Cell cycle assay was performed in order to understand the role of SPB-NPson cancer cell division regulation. SKOV3 and B16 cells were treated with SPB$_{(1,1)}$NPs (30-µM) for 24 hours and washed with DPPS for 2 times and fixed in 70% ethanol and kept in -20 for 24 hours. Cells were rehydrated with DPPS and stained with PI (100 µg/mL) and RNase (50 µg/ml) mixture for 45 minutes at room temperature. Using FACScan flow cytometer (BD bioscience) DNA content was measured. Histogram was collected for gated population and named as sub-G1, G0/G1, S, and G2 phase. The cell cycle approach tells distribution of cells in four major phases of the cycle (G0 vs G1 vs S vs G2/M). Cell cycle assay results shows that in case of B16F10 melanoma cancer the cells have been arrested in the sub-G1 and S phase in the SPB$_{(1,1)}$NPs treated cells whereas, in case of SKOV3 cells G2/M phase arrest occurs (FIG. 9.a-d & FIG. 10.a-e). So it is clearly visible that SPB$_{(1,1)}$NPs can show multimode cell cycle regulatory action.

Example-13: Immunoblotting Assay

Figure 11:
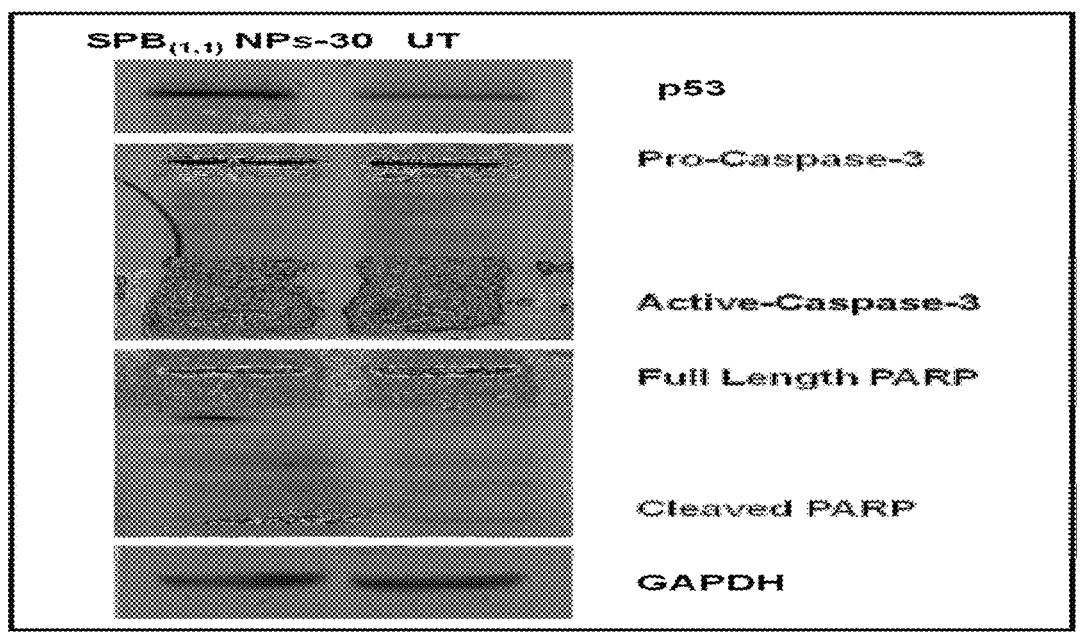
FIG. 11: Western blot analysis result shows the upregulation of p53, active caspase3 and cleaved PARP in the $SPB_{(1,1)}$NPs treated B16F10 cancer cells.

This example illustrates the protein expression in B16 cells for the effect of silver analog Prussian blue nanoparticles (SPB$_{(1,1)}$-NPs) in various human and mouse cancer cells. The synthesis of SPB$_{(1,1)}$-NPs was done as explained in example-2. For the analysis of protein expression in B16 cells immunoblot experiment was carried out. The B16 cells were seeded in the 100 mm dishes and cultured till the cell confluency reaches to 70%. The synthesized SPB$_{(1,1)}$NPs were treated at 30 μM concentration and incubated for 24 hours. Protein samples were prepared by using the RIPA (Radio immuno precipitation assay buffer) with protease inhibitor cocktail. The total protein concentration was determined by using Bradford assay. The samples were electrophoresed in 15% SDS-PAGE and blotted on to the PVDF membrane. Nonspecific portions of proteins were blocked by incubating with 5% BSA for 1.30 hours and washed thrice with TBST (tris buffered saline with tween 20). The membrane was then incubated with respective primary antibodies i.e., p53, PARP (poly ADP ribose polymerase), Caspase-3, GAPDH (dilutions were followed according to the manufactures instructions) for 2 hours and again washed with TBST solution for thrice. The membrane was incubated with alkaline phosphatase conjugated secondary antibody for 1 hour and developed with BCIP solution. Immunoblotting analysis in B16 cell line was showed the up regulation of p53 protein in SPB$_{(1,1)}$NPs treated sample compared to control. This was indicated that the apoptosis pathway is operated by the activation of tumor suppressor protein p53 and resulted in the caspase 3 and PARP cleavage (FIG. 11).

Example-14: Analysis of Nuclear Damage by Hoechest Staining

Figure 12:
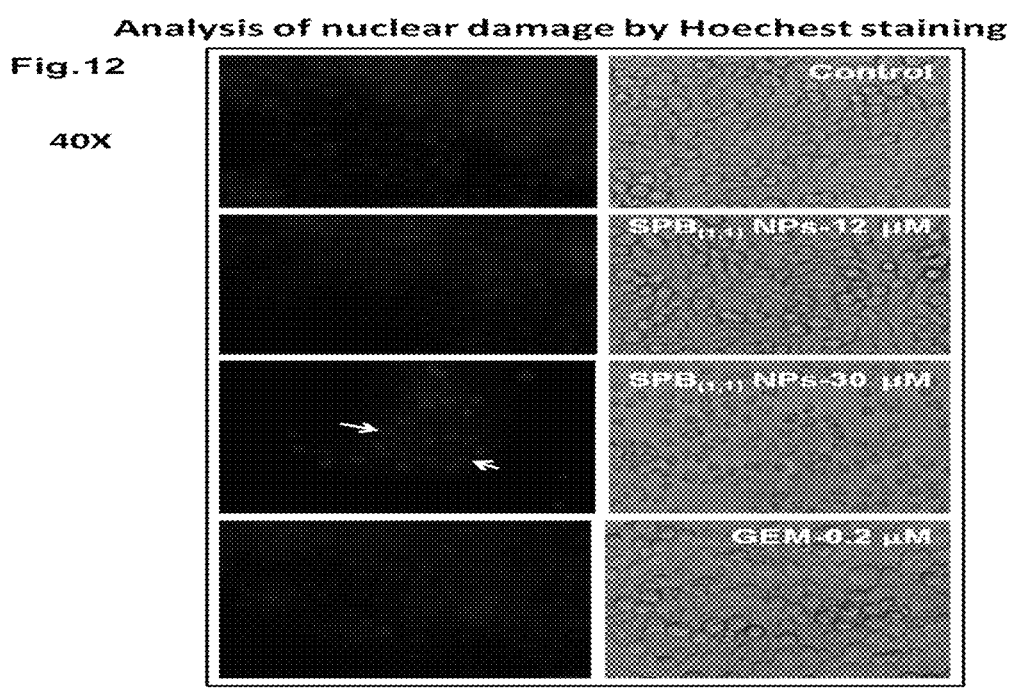
FIG. 12: Analysis of nucleus of untreated and $SPB_{(1,1)}$NPs treated SKOV3 cells by Hoechest staining. Results show the nuclear fragmentation marked by white arrow in $SPB_{(1,1)}$ NPs treated SKOV3 cancer cells indicate the nuclear damage or tendency of cellular apoptosis.

Nuclear damage was analyzed by Hoechest staining with SKOV3 cell line. 24 well plate was seeded with SKOV3 cell and incubated for 24 hours. The SPB$_{(1,1)}$NPs were treated with 30 μM concentration and further incubated for 6 hours. The nucleus was stained by using Hoechest for 30 minutes and washed with DPBS for 3-4 times. Fluorescence pictures were collected with excitation at 356 nm and emission at 465 nm. From the observation of the untreated and SPB$_{(1,1)}$NPs treated nucleus it is clearly evident that there is several damage occurs in the SPB$_{(1,1)}$NPs treated nucleus due to the DNA damage and apoptosis (FIG. 12).

Example-15: Cell Migration Inhibition Assay

Figure 13:
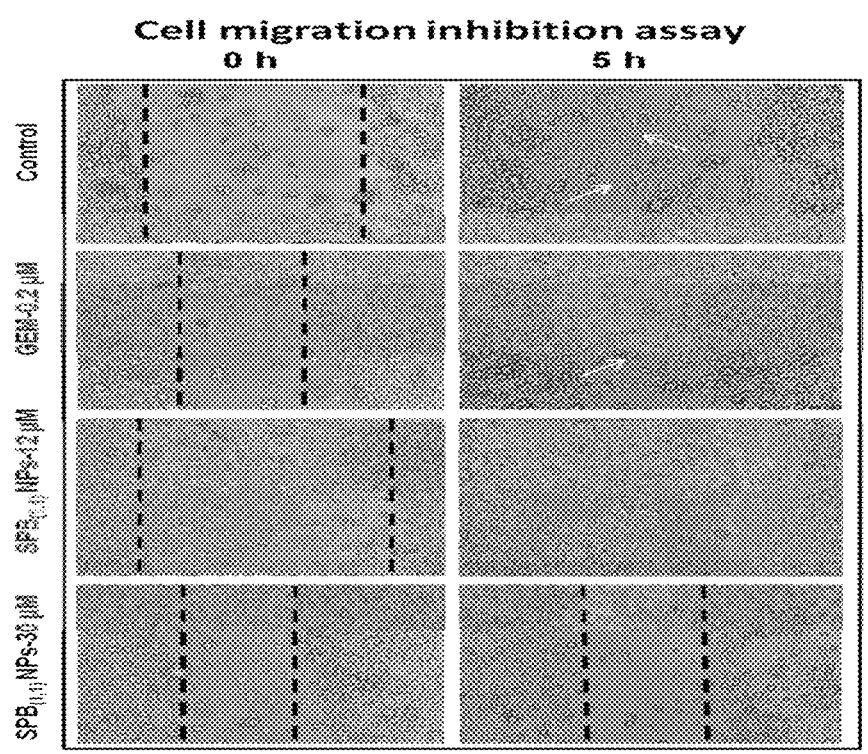
FIG. 13: Wound healing or scratching assay of $SPB_{(1,1)}$ NPs in SKOV3 cells. Result shows the $SPB_{(1,1)}$NPs treated cells inhibit the healing of wound.

This example illustrates the cell migration inhibition effect of silver analog Prussian blue nanoparticles (SPB$_{(1,1)}$-NPs) in human ovarian metastatic cancer cells (SKOV3). The synthesis of SPB$_{(1,1)}$-NPs was done as explained in example-2. To understand the role of SPB$_{(1,1)}$NPs on cancer cell growth kinetics, cell migration inhibition assay was performed. SKOV3 cells were seeded in 24 well plates and incubated for 24 hours. A gap was created by scratching the cell monolayer with fine edge of plastic tip. Cells were washed with PBS and fresh media was added. The pellet of SPB$_{(1,1)}$NPs were treated with SKOV3 cells and incubated for 5 hours. Simultaneously, the anticancer drug gemcitabine with GEM-0.2 μM was used as positive control. Cancer cell migration inhibition is required during the control of tumor aggressiveness to prevent from the metastasis condition. It is clearly indicating that SPB$_{(1,1)}$NPs inhibiting the cell migration when compared to control. After 6 hours of incubation the SKOV3 cells again migrated towards the scratched area but the SPB$_{(1,1)}$NPs treated cells unable to migrate due to the cytotoxic as well as migration inhibition activity of SPB$_{(1,1)}$NPs (FIG. 13).

Example-15: In Vivo Tumor Model in C57BL6/J Mice

Figure 14:
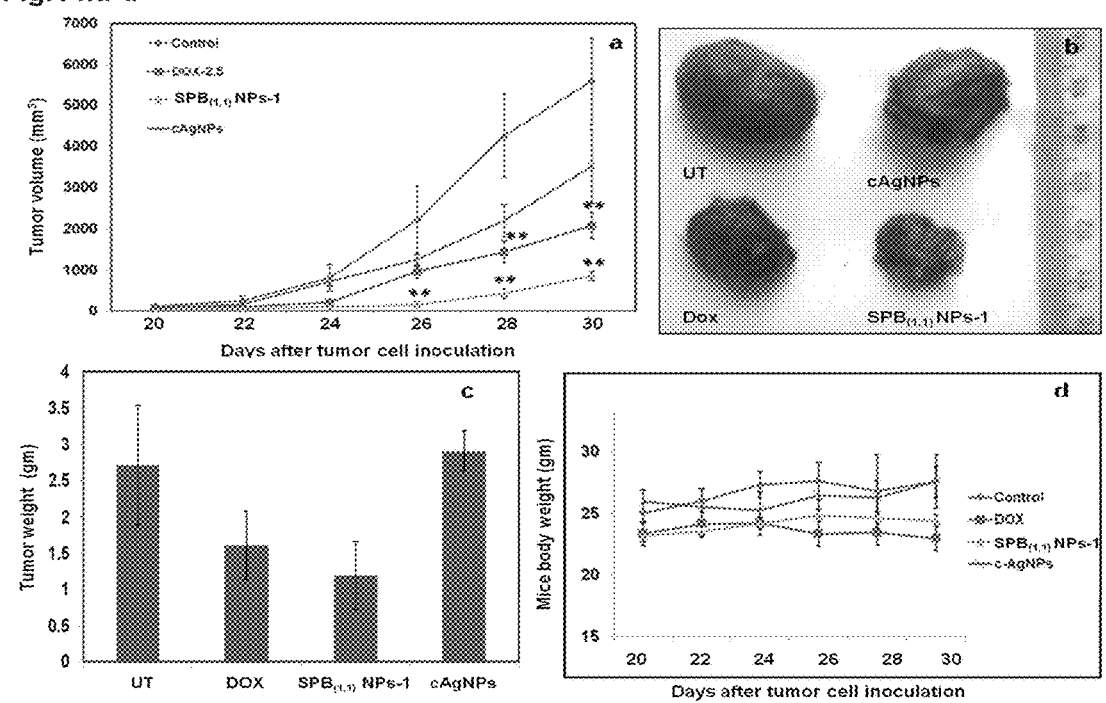
FIG. 14.*a-d*: In vivo allograft mice (C57BL6/J) tumor model. (a) Tumor regression study of $SPB_{(1,1)}$NPs after intraperitoneal administration of DOX, $SPB_{(1,1)}$NPs (1 mg/kg) and cAgNPs (1 mg/kg)/untreated (UT) mice after subcutaneous inoculation of B16F10 cell in C57BL6/J mice. Results indicate that Ag—Fe NPs has higher tumor inhibition effect than DOX or cAgNPs. [** represents p<0.05], (b) optical image of tumors untreated and treated with DOX, $SPB_{(1,1)}$NPs (1 mg/kg) and cAgNPs (1 mg/kg) after sacrifice of C57BL6/J mice, (c) weight of the tumors represented as a bar diagram after the sacrifice, (d) time dependent body weight of all untreated and treated mice.

This example illustrates the in vivo antitumor effect of silver analog Prussian blue nanoparticles (SPB$_{(1,1)}$-NPs) towards aggressive murine melanoma model in C57BL6/J mice. The synthesis of SPB$_{(1,1)}$-NPs was done as explained in example-2. In vivo tumor model was carried out using male C57BL6/J mice (8-9 weeks old). Approximately, 2.5×10$^5$ B16F10 cells resuspended in 100 μL of sterile HBSS were subcutaneously injected to lower right abdomen of male mice. When tumor volume reached 50-100 mm$^3$ after ~14-18 days of injection of B16F10 cells, the mice were randomly divided into four groups (each contains five mice (n=5)) such as Gr-1: untreated control group, Gr-II: mice treated with free Dox (2.5 mg/kg), Gr-III: mice treated with SPB$_{(1,1)}$NPs (1 mg/kg) and Gr-IV: mice treated with chemically synthesized AgNPs i.e. cAgNPs (1 mg/kg). All the treatments were Intraperitoneally (IP) injected on alternate days over a period of 15 days. The volume of tumor was measured by using the formula (0.5×ab$^2$), where 'a' represents the longest dimension and 'b' represents the shortest dimension of the tumors. Also, the weight and picture of the tumors were taken after the sacrifice. Investigation of in vitro functional activity of SPB$_{(1,1)}$NPs in different cancer cells encourages us to perform the therapeutic efficacy of these nanoparticles towards aggressive murine melanoma mice model. The tumor bearing mice have been treated with free Dox (2.5 mg/kg), SPB$_{(1,1)}$NPs (1 mg/kg) and chemically synthesized AgNPs i.e. cAgNPs (1 mg/kg) to check the tumor regression efficiency of SPB$_{(1,1)}$NPs. It is evident from FIG. 14.a, mice treated with SPB$_{(1,1)}$NPs (1 mg/kg) show significant reduction of tumor volume compared to those mice treated with free Dox, cAgNPs and untreated mice with time. The optical picture of FIG. 14.b indicates the representative tumor volume of untreated mice & mice treated with free Dox, cAgNPs and treated with SPB$_{(1,1)}$NPs. The picture shows the huge reduction of tumor volume in mice treated with SPB$_{(1,1)}$NPs compared to untreated mice, cAgNPs and free Dox treated mice. Tumor weight data also showed that tumor treated with SPB$_{(1,1)}$NPs has least weight compared to tumors of untreated mice, cAgNPs and free Dox treated mice (FIG. 14.c). It is also observed that after four intraperitoneal (IP) injections, mice treated with only free Dox shows significant loss of bodyweight compared to mice treated with SPB$_{(1,1)}$NPs (FIG. 14.d). The loss of body weight can correlate with the nonspecific side effects of Dox in normal physiological function.

Example-16: Western Blotting Using Tumor Lysate

Tumor Lysate Preparation:
B16F10 melanoma tumor from treated animals was freshly collected after scarifying the mice and kept in ice cold PBS. The upper skin was carefully removed and washed with PBS for 3 times. The tumor tissue was chopped into small pieces and 500 μl of RIPA buffer with protease inhibitor cocktail was added. The tissue was homogenized by keeping on ice. The lysate then centrifuged at 12000 rpm for 30 minutes and the supernatant was collected for protein expression analysis.

Figure 15:
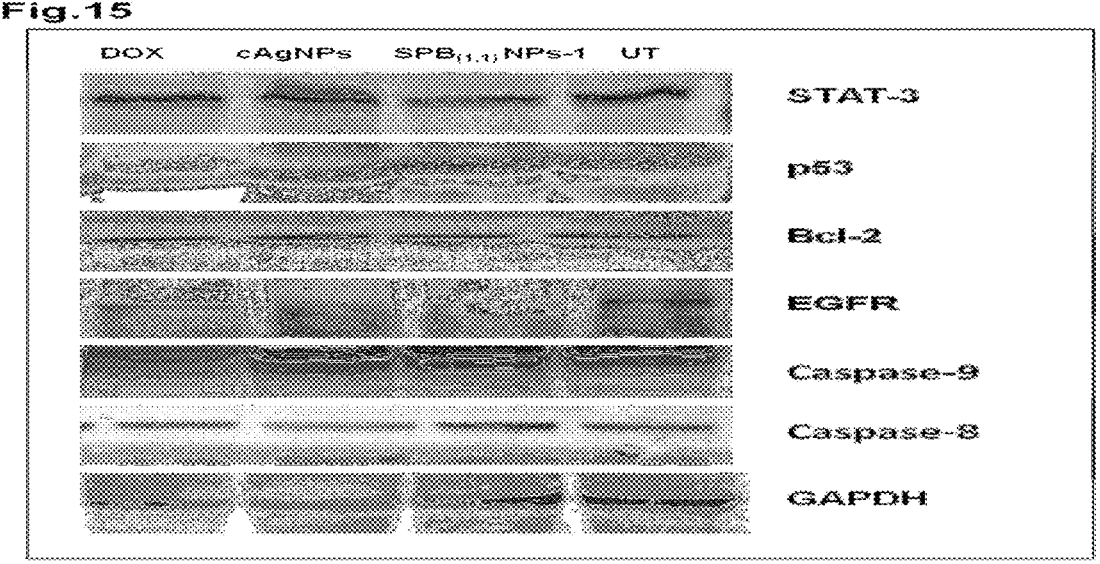
FIG. 15: Western blot analysis with tumor protein lysates shows the upregulation of p53, caspase 8 and caspase 9 and down-regulation of Bcl-2, stat-3 and EGFR proteins in the $SPB_{(1,1)}$NPs treated tumor protein lysates.

Western Blotting Using Tumor Lysate:
Total protein concentration in the tumor lysate was estimated by Bradford method and the protein samples were resolved in 15% SDS-PAGE. After the electrophoretic separation the proteins were immobilized on to the PVDF membrane. 5% BSA was used to block the nonspecific sites of the blotted proteins and incubated with anticaspase-3, BCL2, PARP, Capspae-9, caspase-7, caspase-8, STAT-3, EGFR, p53, GAPDH antibodies for overnight at 4° C. The membrane was washed with TBST solution for 3 times followed by incubation with alkaline Phosphatase conjugated secondary antibody solution for 1 hour at room temperature. The membrane was developed with BCIP/NBT solution in dark until protein bands appear on the membrane. Western blot results of tumor lysate have revealed the molecular mechanism involved the SPB$_{(1,1)}$NPs induced cell death. Particularly the SPB$_{(1,1)}$NPs treated tumor lysate showed the apoptotic protein expression compared to cAg-NPs and positive control. The p53 protein was up regulated in SPB$_{(1,1)}$NPs treated sample with down regulation of STATS and EGFR expression which could be the main reason for the induction of cell death via apoptosis pathway (FIG. 15). NiuG et al has been discussed that p53 transcription rate was inhibited by the stat3 protein by binding to the p53 promoter region in the DNA (Niu G et al, Mol Cell Biol. 2005; 25: 7432-7440). Down regulation of stat3 resulted the activation of p53 and caused the apoptotic cell death. In our experiments also the stat3 downregulated and caused the p53 up regulation.

Example-17: Antibacterial Activity

This example illustrates the antibacterial effect of silver analog Prussian blue nanoparticles (SPB$_{(1,1)}$-NPs) towards *E. coli* and *Bacillus subtilis*. The synthesis of SPB$_{(1,1)}$-NPs was done as explained in example-2.

Figure 16:
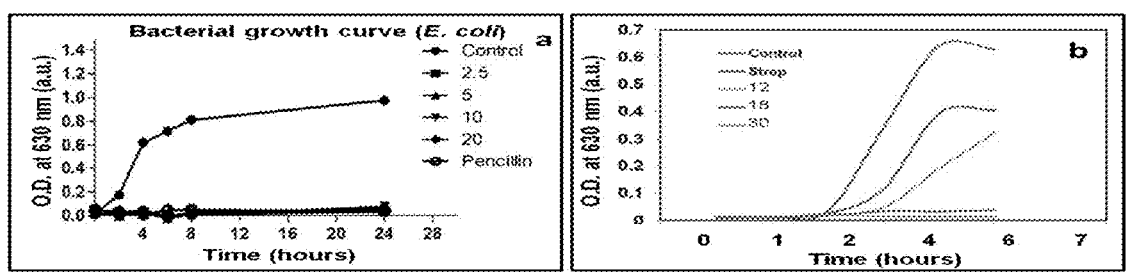
FIG. 16: Growth inhibition of *E. coli* in presence of $SPB_{(1,1)}$NPs. Results shows that minimum inhibitory concentration (MIC) of $SPB_{(1,1)}$NPs is 30 μM. Numerical values indicates the silver concentrations in μM.

Determination of Minimum Inhibitory Concentration (MIC) of SPB$_{(1,1)}$NPs:

Bacterial growth inhibition assay was performed according to our previously published work (Mukherjee et al. Theranostics, 2014; 4: 316-335). Briefly, Luria Bertani broth was utilized to determine the bacterial growth inhibition by the SPB$_{(1,1)}$NPs. After reaching the bacterial cell density up to 0.6, it was inoculated into the 5 ml of fresh LB broth and incubated at 37° C. at 180 rpm SPB$_{(1,1)}$NPs were added to the pre-inoculated LB broth and the growth conditions were maintained. At regular intervals the O.D of the bacterial cultures were checked at 630 nm up to 7 hours. Bacterial media without culture as blank, culture with media as control, bacterial culture with penicillin (2 mg/ml) as positive control and SPB$_{(1,1)}$NPs at different concentrations were taken as treatment groups. To identify the inhibitory action of SPB$_{(1,1)}$NPs on bacterial growth we performed the bacterial growth inhibition assay. We have identified that as-synthesized SPB$_{(1,1)}$NPs show significant growth inhibition at 30 µM concentration (FIG. 16.a-b) where the control set bacteria grown normally and showed the sigmoid curve. The same type of result was observed in the positive control streptomycin set.

Figure 17:
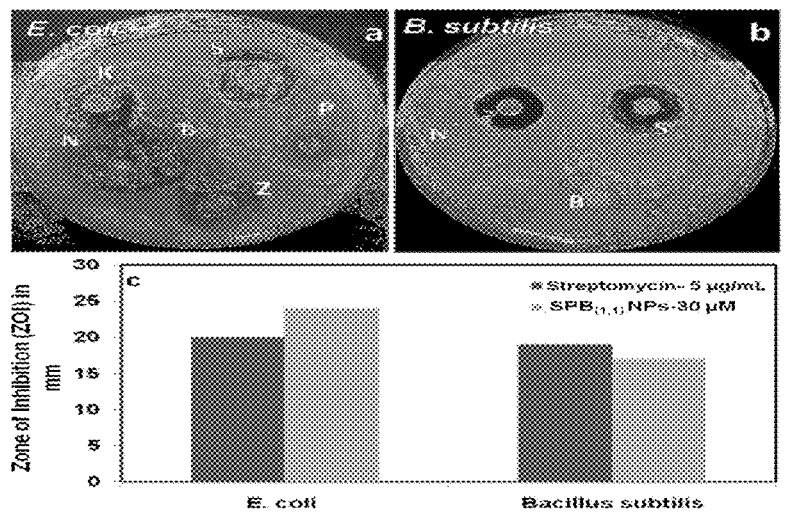
FIG. 17: Zone of inhibition of *E. coli* and *Bacillus subtilis* treated with $SPB_{(1,1)}$NPs and standard antibiotics in agar plate. Result shows significant inhibition zone in $SPB_{(1,1)}$ NPs treated samples.

Example-18: Agar Disc Diffusion Method on Gram Positive and Gram Negative Bacteria To determine the antimicrobial activity of SPB$_{(1,1)}$NPs we have performed the agar disc diffusion method on both Gram negative (*E. coli*) and Gram positive (*Bacillus subtilis*) bacteria. Initially LB agar plates were prepared at aseptic conditions and inoculated with freshly grown (O.D. around at 0.6) *E. coli* and *Bacillus subtilis*. Pre-sterilized whatmann no. 1 filter paper discs were prepared and soaked in the SPB$_{(1,1)}$NPs solution and different antibiotic solutions at 1 mg/ml concentration (streptomycin, kanamycin, penicillin, and gentamicin), for 15 minutes and placed on the surface of the agar plates. The plates were incubated at 37° C. for 24 hours. The zone of inhibition of as synthesized SPB$_{(1,1)}$NPs in both Gram negative (*E. coli*) and Gram positive (*Bacillus subtilis*) bacteria have been determined using the agar disc diffusion method. Ag—Fe NPs treated samples showed almost 24 mm & 21 mm inhibition zone with respect to *E. coli* and *Bacillus subtilis* strains. Of these two strains, zone of inhibition was more when compared to standard antibiotics like kanamycin, streptomycin, gentamycin, penicillin. Interestingly, the inhibitory zone of SPB$_{(1,1)}$NPs was prolonged up to 48 hours (FIG. 17.a-c).

Example-19: Determination of Colony Forming Units (CFU)

Figure 18:
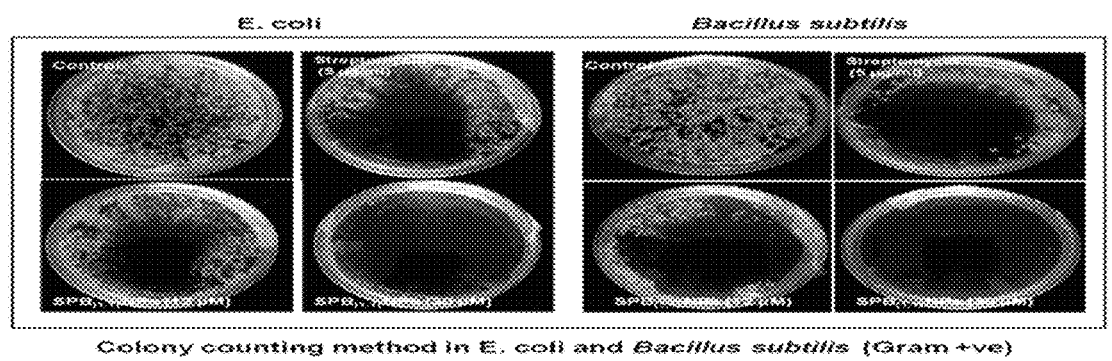
FIG. 18: Optical images of bacterial colony formed by *E. coli* and *Bacillus subtilis* after 24 hours in untreated, streptomycin (5 μg/ml) and $SPB_{(1,1)}$MPs (12 & 30 μM) treated samples.

This example illustrates the antibacterial effect of silver analog Prussian blue nanoparticles (SPB$_{(1,1)}$-NPs) towards *E. coli* and *Bacillus subtilis*. The synthesis of SPB$_{(1,1)}$-NPs was done as explained in example-2. The LB agar medium was spread with 30 µM concentration of SPB$_{(1,1)}$NPs and after with freshly grown *E. coli* and *Bacillus subtilis* (O.D. around 0.6). Streptomycin at 2 mg/ml concentration was used as positive control. The plated were incubated for 24 hours at 37° C. The number of colonies appeared on the surface of the LB agar plates were counted. Colony forming unit is an indirect method for determination of antimicrobial activity of SPB$_{(1,1)}$NPs. There was complete inhibition of bacterial growth when treated with SPB$_{(1,1)}$NPs at 30 µM concentration. But bacterial colonies were observed on positive control. We previously reported the antibacterial activity of biosynthesized silver nanoparticles (Mukherjee et al. Theranostics, 2014; 4: 316-335). Likewise in our current investigation also, SPB$_{(1,1)}$NPs given the complete inhibition of both Gram negative (*E. coli*) and Gram positive (*Bacillus subtilis*) bacterial growth after 24 hours (FIG. 18).

Example-20: Analysis of Soil Bacterial Growth Inhibition by SPB$_{(1,1)}$ NPs

Figure 19:
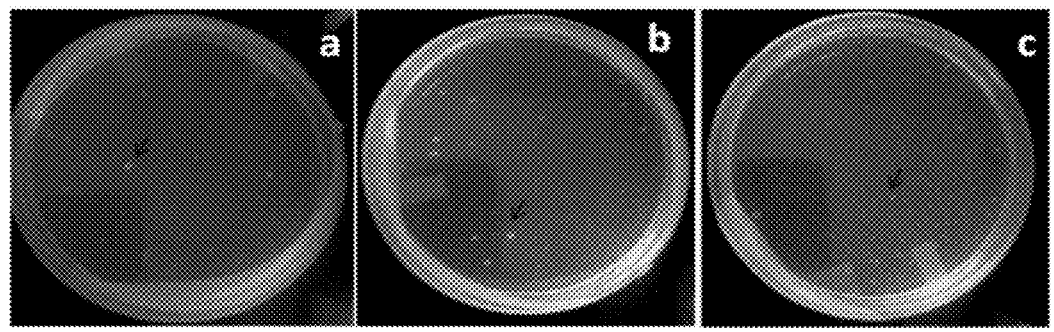
FIG. 19: Optical images of inhibition of soil bacteria growth by $SPB_{(1,1)}$NPs (30 μM) and streptomycin (5 μg/ml). Results shows almost complete inhibition of soil bacteria in case of $SPB_{(1,1)}$NPs treated soil.

To analyze the effect of SPB$_{(1,1)}$NPs on soil grown bacteria, we have performed the serial dilution method where we have taken the 1 gram of soil and dissolved in the 10 ml of distilled water. This soil sample was diluted for further six times with sterile distilled water. The last sixth portion was taken and inoculated on the LB agar plate using spread plate method and incubated for 24 hours. The serial dilution method was the basic technique in the microbiology to isolate the pure colonies of bacteria from the soil sample. This method can also give the chance to culture different bacteria on single agar plate. This was enabled us to see the effect of SPB$_{(1,1)}$NPs on soil living bacteria. Interestingly, there was significant growth inhibition in SPB$_{(1,1)}$NPs treated plate compared to control (FIG. 19.a-c). This assay giving the idea that SPB$_{(1,1)}$NPs are not only showing the antibacterial effect on specific strains of bacteria, but also inhibited the growth of all different wild type bacteria. This broad range antibacterial activity of as-synthesized silver nanoparticles will be helpful for the coating materials in biological implants.

Example-21: Antibacterial Mechanism

This example illustrates the mechanism for antibacterial effect of silver analog Prussian blue nanoparticles (SPB$_{(1,1)}$-NPs) towards *E. coli* and *Bacillus subtilis*. The synthesis of SPB$_{(1,1)}$-NPs was done as explained in Example-2.

Preparation of Bacterial Cell Lysate:

Initially, 5 ml of freshly grown culture of E. coli was taken and treated with 30 μM concentration of $SPB_{(1,1)}$NPs and 2 mg/ml concentration of streptomycin. The culture was then incubated for 4 hours under shaking. The incubated bacterial cells were centrifuged at 15 minutes at 6000 rpm at 4° C. Bacterial cell pellet was suspended in lysis buffer followed by addition of lysozyme and incubate at 4° C. for 4 hours. Cell debris was removed by centrifugation at 12000 rpm for 30 minutes. The resulted supernatant was used for biochemical analysis. A SDS PAGE gel was run to understand the change in protein expression.

Activity Staining of Catalase:

To analyze the effect of $SPB_{(1,1)}$NPs on the bacterial catalase enzyme in bacteria, activity staining was performed on 6% the non-denaturing poly acrylamide gel. The protein samples without beta mercaptoethanol were electrophoresed in tris-glycine buffer without SDS in 4° C. After the separation, the gel was incubated in 0.01% of $H_2O_2$ solution for 10 minutes and followed by staining with the solution containing 2% $FeCl_3$ and $K_3Fe(CN)_6$.

Assay of Superoxide Dismutase:

The assay of superoxide dismutase was performed according the method of Beauchamp and Fridovich (Beauchamp et al. Anal. Biochem. 1971; 44: 276-287) based on the reduction of Nitrobluetetrazolium (NBT). Briefly, 100 μl of cell lysate, 200 μl of sodium carbonate, 80 μl of 24 μM NBT and 40 μl of 0.1 mM EDTA were mixed at room temperature. The reaction was initiated by the addition of 80 μl of 1 mM hydroxylamine hydrochloride. The reaction mixer was than analyzed by taking the O.D. at every 30 seconds up to 3 minutes. Simultaneously blank was taken without cell lysate. Units of SOD were expressed as amount of enzyme required for inhibiting the reduction of NBT by 50%. The specific activity was expressed in terms of units per milligram of protein.

Measurement of Lipid Peroxidation:

Lipid peroxidation was measured according to standard protocol. Initially 0.5 ml of bacterial cell suspension was treated with 30 μM concentration of $SPB_{(1,1)}$NPs and incubated for 30 minutes at room temperature. 1.5 ml of 20% acetic acid (pH 3.5), 1.5 ml of 0.8% thiobarbituric acid (in 1.1% SDS) and 0.05 ml of 20% TCA were added and mixed thoroughly. The tubes were then incubated for 60 minutes at 100° C. and 5 ml of butanol was added to each tube. The tubes were then centrifuged at 4000 rpm for 15 minutes. The pink supernatant was measures at 532 nm. The % of lipid peroxidation was measured by using the following formula: % of lipid peroxidation=(sample O.D/Control O.D)×100.

Figure 20:
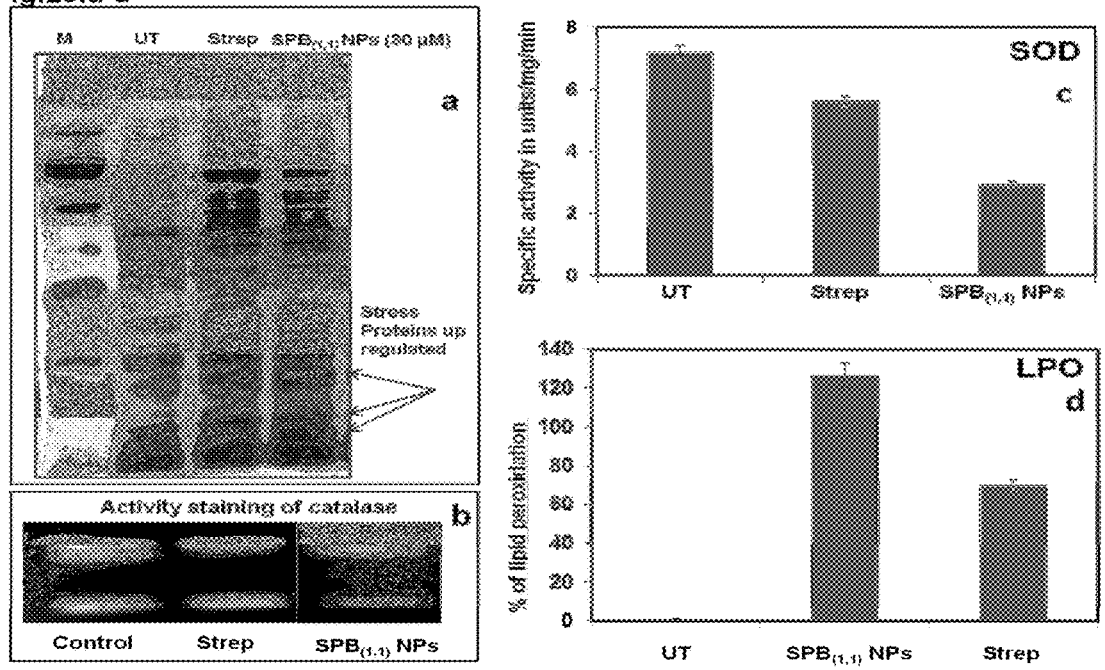
FIG. 20: Lipid peroxidation assay (LPO), superoxide dismutase (SOD) and catalase staining assay of $SPB_{(1,1)}$NPs treated *E. coli*. Results show the depletion of SOD and catalase and enhancement of LPO levels in $SPB_{(1,1)}NPs$ treated samples.

From SDS-PAGE gel run it is clear the some stress related proteins or shock proteins are upregulated upon the exposure of $SPB_{(1,1)}$NPs to the bacteria (FIG. 20.a).

Activity Staining of Catalase:

The antioxidant enzyme catalse plays a vital role in the removal of hydroxyl radicals from the cell in oxidative stress conditions. During the exposure of $SPB_{(1,1)}$NPs to the bacteria, silver nanoparticles will penetrate into the bacterial cell and creates the reactive oxygen species which results in the oxidative burst of the cell (FIG. 20.b). In some conditions silver ions also may generate from the silver nanoparticles, which also play role in the cytotoxic activity of silver nanoparticles. Such type of free radicals results in the decrease in the antioxidant enzyme levels. In the current study also the catalse enzyme activity is going down in the $SPB_{(1,1)}$NPs treated bacteria cells compared to control which might be the possible reason for bacterial cell death. Bioinformatics structure prediction studies on the catalse enzyme and silver nanoparticles were revealed that silver nanoparticles interact with the bacterial catalase enzyme, which is the main reason for the decrease in its activity. From our previous studies it is very clear that decrease in the bacterial catalse enzyme is the main event occurs in the bacteria during silver nanoparticle mediated cell death.

Assay of Superoxide Dismutase:

Superoxide dismutase mainly involves in the dismutation of superoxide radicals in the cells. Decreased levels of cellular antioxidant system, increases the reactive oxygen species in the cell, which leads to the cell death. In our current study also, the SOD enzyme levels are went down in the bacterial lysate treated with 30 μM concentration of $SPB_{(1,1)}$NPs (2.94 units/mg protein) compared to control cell lysate (10.66 units/mg protein) (FIG. 20.c). This study was clearly indicating that the internalized $SPB_{(1,1)}$NPs creating the oxidative stress which could be the possible reason for the bacterial cell death.

Measurement of Lipid Peroxidation:

To determine the membrane damage by the $SPB_{(1,1)}$NPs, lipid peroxidation measurement was performed. $SPB_{(1,1)}$NPs treated bacterial lysate showed the more lipid peroxidation (120%) compared to the positive control (60%) (FIG. 20.d). This investigation supports our hypothesis that the cellular oxidative stress contributes the membrane damage, which leads to the cell death.

ADVANTAGES

The SPB-NPs are highly stable for more than two weeks towards different physiological buffers or solutions with different pH. These nanoparticles (SPB-NPs) exhibit biocompatibility towards various normal cells but show significant inhibition of proliferation of different cancer cells in vitro and tumor growth in C57/BL6/J mice model. Additionally, the SPB-NPs show excellent antibacterial activity towards gram-negative (E. coli) and gram-positive (B. subtilis) bacteria. Consider all results together; these biocompatible SPB-NPs would be potentially useful for the development towards alternative anti-cancer agent as well as anti-bacterial agent in near future.

We claim:

1. A material comprising polymer coated nanoparticles of a Prussian blue material formed of cubic crystalline biocompatible silver Prussian blue ($Ag_3[Fe(CN)_6]$), wherein the nanoparticles each have an outer surface with a polymer coating applied to the outer surface such that the polymer coating directly contacts the Prussian blue material over an entirety of the outer surface, the polymer coating including one or more polymers comprising PVP (poly(N-vinyl-2-pyrrolidone)), wherein the nanoparticles have spherical shapes, and a particle size of the nanoparticles is in a range of 5-40 nm, and wherein the material is provided by mixing a solution of $AgNO_3$ and $K_3Fe(CN)_6$ in a 1:1 molar ratio and mixing the solution with a polymer solution comprising PVP.

2. The material as claimed in claim 1, wherein the nanoparticles are an anti-cancer agent that shows cytotoxicity towards several cancer cells in vitro and inhibition of tumor growth in vivo model.

3. The material as claimed in claim 1, wherein the nanoparticles exhibit antibacterial activity in gram-negative bacteria as well as gram-positive bacteria at a concentration of silver in a range of 10-30 μM.

4. The material as claimed in claim 1, wherein the nanoparticles exhibit in vitro anti-cancer activity of nanoparticles in different cancers including ovarian cancer, breast cancer, lung cancer and melanoma cancers at a concentration of silver in a range of 10-30 µM.

5. The material as claimed in claim 1, wherein the nanoparticles exhibit reduction in tumor growth towards in vivo melanoma tumors when administered alone in an in vivo murine model.

6. The material as claimed in claim 1, wherein the nanoparticles are configured for use as an anti-metastatic agent.

7. The material as claimed in claim 1, wherein the one or more polymers further include PEG (polyethylene glycol).

8. The material as claimed in claim 3, wherein the nanoparticles exhibit the antibacterial activity in gram-negative E. coli bacteria as well as gram-positive B. subtilis bacteria at the concentration of silver in the range of 10-30 µM.

9. The material as claimed in claim 1, wherein said nanoparticles exhibit high biocompatibility in various in vitro and in vivo mice models.

10. The material as claimed in claim 1, wherein said nanoparticles exhibit better anti-cancer and anti-bacterial activity compared to silver nanoparticles at a dose range of 10-30 µM.

11. The material as claimed in claim 1, wherein said nanoparticles exhibit both anti-cancer and anti-bacterial activity.

12. A therapeutic treatment preparation comprising polymer coated nanoparticles of a Prussian blue material formed of cubic crystalline biocompatible silver Prussian blue ($Ag_3[Fe(CN)_6]$), wherein the nanoparticles each have an outer surface with a polymer coating applied to the outer surface such that the polymer coating directly contacts the Prussian blue material over an entirety of the outer surface, the polymer coating including one or more polymers, wherein the nanoparticles have spherical shapes, and a particle size of the nanoparticles is in a range of 5-40 nm, wherein the one or more polymers comprise PVP (poly(N-vinyl-2-pyrrolidone)), and wherein the nanoparticles are present in the treatment such that the treatment has a silver concentration of 10-90 µM, and wherein the material is provided by mixing a solution of $AgNO_3$ and $K_3Fe(CN)_6$ in a 1:1 molar ratio and mixing the solution with a polymer solution comprising PVP.

13. The therapeutic treatment of claim 12, wherein the nanoparticles are present in the treatment such that the silver concentration of the treatment is 10-30 µM.

14. A material comprising polymer coated nanoparticles of a Prussian blue material formed of cubic crystalline biocompatible silver Prussian blue ($Ag_3[Fe(CN)_6]$), wherein the nanoparticles each have an outer surface with a polymer coating comprising PVP (poly(N-vinyl-2-pyrrolidone)) applied to the outer surface such that the PVP directly contacts the Prussian blue material over an entirety of the outer surface, wherein the nanoparticles have spherical shapes, and a particle size of the nanoparticles is in a range of 5-40 nm, and wherein the material is provided by mixing a solution of $AgNO_3$ and $K_3Fe(CN)_6$ in a 1:1 molar ratio and mixing the solution with a polymer solution comprising PVP.

15. The material as claimed in claim 14, wherein the polymer solution comprises 1% PVP, and 4-4000 µL of the polymer solution is mixed in providing the material.

16. The material as claimed in claim 14, wherein the nanoparticles are configured for use as an anti-metastatic agent.

17. The material as claimed in claim 14, wherein the one or more polymers further include PEG (polyethylene glycol).

18. The material as claimed in claim 14, wherein the nanoparticles exhibit biocompatibility and reduction in tumor growth towards in vivo melanoma tumors when administered alone in an in vivo murine model.

19. The material as claimed in claim 1, wherein the polymer solution comprises 1% PVP, and 4-4000 µL of the polymer solution is mixed in providing the material.

20. The material as claimed in claim 1, wherein the polymer coating is applied to the outer surfaces of the nanoparticles such that the PVP directly contacts the Prussian blue material over the entirety of the outer surface.

\* \* \* \* \*